US010835153B2

(12) United States Patent
Rafii-Tari et al.

(10) Patent No.: US 10,835,153 B2
(45) Date of Patent: Nov. 17, 2020

(54) SYSTEM AND METHOD FOR MEDICAL INSTRUMENT NAVIGATION AND TARGETING

(71) Applicant: Auris Health, Inc., Redwood City, CA (US)

(72) Inventors: Hedyeh Rafii-Tari, Mountain View, CA (US); Prasanth Jeevan, San Mateo, CA (US); Douglas T. Boyd, Soquel, CA (US); Melissa A. Teran, Redwood City, CA (US); Alexander James Sheehy, Redwood City, CA (US); Nicolas E. Robert, San Leandro, CA (US); Miroslav Drahos, Freehold, NJ (US); Jeffery D. Howard, San Francisco, CA (US); Andrew Esbenshade Zeldis, Berkeley, CA (US); René Ango Mambembe, Nantes (FR)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/212,495

(22) Filed: Dec. 6, 2018

(65) Prior Publication Data

US 2019/0175062 A1 Jun. 13, 2019

Related U.S. Application Data

(60) Provisional application No. 62/596,710, filed on Dec. 8, 2017.

(51) Int. Cl.
*A61B 5/00* (2006.01)
*A61B 5/06* (2006.01)
(Continued)

(52) U.S. Cl.
CPC .............. *A61B 5/066* (2013.01); *A61B 34/20* (2016.02); *A61B 34/25* (2016.02); *A61B 34/30* (2016.02);
(Continued)

(58) Field of Classification Search
CPC ......... A61B 5/066; A61B 90/37; A61B 34/74; A61B 2034/2051; A61B 2034/301;
(Continued)

(56) References Cited

U.S. PATENT DOCUMENTS 4,771,262 A 9/1988 Reuss
4,896,554 A 1/1990 Culver
(Continued)

FOREIGN PATENT DOCUMENTS

EP 1 800 593 6/2007
EP 2 158 834 3/2010
(Continued)

OTHER PUBLICATIONS

International Search Report and Written Opinion in application No. PCT/US2018/64357, dated Feb. 5, 2019.

*Primary Examiner* — Joel Lamprecht
(74) *Attorney, Agent, or Firm* — Knobbe, Martens, Olson & Bear, LLP

(57) ABSTRACT

Certain aspects relate to systems and techniques for medical instrument navigation and targeting. In one aspect, a system includes a medical instrument having an elongate body and at least one sensor, a display, a processor, and a memory storing a model of a mapped portion of a luminal network and a position of a target with respect to the model. The processor may be configured to: determine, based on data from the at least one sensor, a position and orientation of a distal end of the medical instrument with respect to the model, and cause, on at least a portion of the display, a
(Continued)

rendering of the model, the position of the target, and the position and orientation of the distal end of the medical instrument. The rendering may be based on a viewpoint directed at the target and different from a viewpoint of the medical instrument.

30 Claims, 32 Drawing Sheets

(51) Int. Cl.
*A61B 34/00* (2016.01)
*A61B 34/30* (2016.01)
*A61B 34/20* (2016.01)
A61B 90/00 (2016.01)
A61B 34/10 (2016.01)
A61B 90/30 (2016.01)
A61B 90/50 (2016.01)
A61B 17/00 (2006.01)

(52) U.S. Cl.
CPC .............. *A61B 34/74* (2016.02); *A61B 90/37* (2016.02); *A61B 2017/00809* (2013.01); *A61B 2034/105* (2016.02); *A61B 2034/107* (2016.02); *A61B 2034/2051* (2016.02); *A61B 2034/2059* (2016.02); *A61B 2034/2061* (2016.02); *A61B 2034/2065* (2016.02); *A61B 2034/256* (2016.02); *A61B 2034/258* (2016.02); *A61B 2034/301* (2016.02); *A61B 2090/306* (2016.02); *A61B 2090/309* (2016.02); *A61B 2090/365* (2016.02); *A61B 2090/368* (2016.02); *A61B 2090/3614* (2016.02); *A61B 2090/372* (2016.02); *A61B 2090/376* (2016.02); *A61B 2090/3762* (2016.02); *A61B 2090/502* (2016.02); *A61B 2217/005* (2013.01); *A61B 2217/007* (2013.01)

(58) Field of Classification Search
CPC .... A61B 2034/2065; A61B 2034/2061; A61B 2034/105; A61B 2090/368
See application file for complete search history.

(56) References Cited

U.S. PATENT DOCUMENTS

| | | | |
|---|---|---|---|
| 5,008,528 A | 4/1991 | Duchon | |
| 5,176,310 A | 1/1993 | Akiyama et al. | |
| 5,280,781 A | 1/1994 | Oku | |
| 5,499,632 A | 3/1996 | Hill et al. | |
| 5,524,180 A | 6/1996 | Wang et al. | |
| 5,526,812 A | 6/1996 | Dumoulin et al. | |
| 5,762,458 A | 6/1998 | Wang et al. | |
| 5,831,614 A | 11/1998 | Tognazzini et al. | |
| 5,899,851 A | 5/1999 | Koninckx | |
| 5,963,770 A | 10/1999 | Eakin | |
| 6,007,550 A | 12/1999 | Wang et al. | |
| 6,016,439 A * | 1/2000 | Acker | A61B 5/06 600/411 |
| 6,038,467 A | 3/2000 | De Bliek et al. | |
| 6,096,004 A | 8/2000 | Meglan et al. | |
| 6,425,865 B1 | 7/2002 | Salcudean et al. | |
| 6,466,198 B1 | 10/2002 | Feinstein | |
| 6,468,265 B1 | 10/2002 | Evans et al. | |
| 6,516,421 B1 | 2/2003 | Peters | |
| 6,690,964 B2 | 2/2004 | Beiger et al. | |
| 6,856,827 B2 | 2/2005 | Seeley et al. | |
| 7,206,627 B2 | 4/2007 | Abovitz | |
| 7,594,925 B2 | 9/2009 | Danek | |
| 8,180,114 B2 | 5/2012 | Nishihara et al. | |
| 8,718,837 B2 | 5/2014 | Wang et al. | |
| 8,971,597 B2 | 3/2015 | Zhao et al. | |
| 9,241,767 B2 | 1/2016 | Prisco et al. | |
| 9,283,046 B2 | 3/2016 | Walker et al. | |
| 9,498,291 B2 | 11/2016 | Balaji et al. | |
| 9,503,681 B1 | 11/2016 | Popescu et al. | |
| 9,504,604 B2 | 11/2016 | Alvarez | |
| 9,561,019 B2 | 2/2017 | Mihailescu et al. | |
| 9,561,083 B2 | 2/2017 | Yu et al. | |
| 9,566,414 B2 | 2/2017 | Wong et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,770,216 B2 | 9/2017 | Brown et al. | |
| 9,788,910 B2 | 10/2017 | Schuh | |
| 9,827,061 B2 | 11/2017 | Balaji et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,123,843 B2 | 11/2018 | Wong et al. | |
| 10,130,427 B2 | 11/2018 | Tanner et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,346,976 B2 * | 7/2019 | Averbuch | G06T 11/203 |
| 10,482,599 B2 | 11/2019 | Mintz et al. | |
| 10,517,692 B2 | 12/2019 | Eyre et al. | |
| 2002/0077533 A1 | 6/2002 | Bieger et al. | |
| 2002/0120188 A1 | 8/2002 | Brock et al. | |
| 2002/0161280 A1 | 10/2002 | Chatenever et al. | |
| 2002/0173878 A1 | 11/2002 | Watanabe | |
| 2004/0047044 A1 | 3/2004 | Dalton | |
| 2004/0263535 A1 | 12/2004 | Birkenbach et al. | |
| 2005/0085714 A1 | 4/2005 | Foley et al. | |
| 2005/0193451 A1 | 9/2005 | Quistgaard et al. | |
| 2005/0222554 A1 | 10/2005 | Wallace et al. | |
| 2006/0079745 A1 | 4/2006 | Viswanathan et al. | |
| 2006/0095022 A1 | 5/2006 | Moll et al. | |
| 2006/0173290 A1 | 8/2006 | Lavallee et al. | |
| 2007/0083098 A1 | 4/2007 | Stern et al. | |
| 2007/0138992 A1 | 6/2007 | Prisco et al. | |
| 2007/0144298 A1 | 6/2007 | Miller | |
| 2007/0185486 A1 | 8/2007 | Hauck et al. | |
| 2008/0027313 A1 | 1/2008 | Shachar | |
| 2008/0033442 A1 * | 2/2008 | Amiot | A61B 17/1746 606/80 |
| 2008/0082109 A1 | 4/2008 | Moll et al. | |
| 2008/0097465 A1 | 4/2008 | Rollins et al. | |
| 2008/0108870 A1 | 5/2008 | Wiita et al. | |
| 2008/0140087 A1 | 6/2008 | Barbagli et al. | |
| 2008/0159653 A1 | 7/2008 | Dunki-Jacobs et al. | |
| 2008/0183068 A1 | 7/2008 | Carls et al. | |
| 2008/0183188 A1 | 7/2008 | Carls et al. | |
| 2008/0306490 A1 | 12/2008 | Lakin et al. | |
| 2009/0248036 A1 | 10/2009 | Hoffman et al. | |
| 2009/0259230 A1 | 10/2009 | Khadem | |
| 2009/0259412 A1 | 10/2009 | Brogardh | |
| 2009/0326322 A1 | 12/2009 | Diolaiti | |
| 2009/0326556 A1 | 12/2009 | Diolaiti et al. | |
| 2010/0019890 A1 | 1/2010 | Helmer et al. | |
| 2010/0039506 A1 | 2/2010 | Sarvestani et al. | |
| 2010/0076263 A1 | 3/2010 | Tanaka | |
| 2010/0121269 A1 | 5/2010 | Goldenberg | |
| 2010/0125284 A1 | 5/2010 | Tanner et al. | |

(56) References Cited

U.S. PATENT DOCUMENTS

| | | |
|---|---|---|
| 2010/0161129 A1 | 6/2010 | Costa et al. |
| 2010/0204613 A1 | 8/2010 | Rollins et al. |
| 2010/0225209 A1 | 9/2010 | Goldberg |
| 2010/0328455 A1 | 12/2010 | Nam et al. |
| 2011/0021926 A1 | 1/2011 | Spencer |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0196199 A1 | 8/2011 | Donhowe et al. |
| 2011/0235855 A1 | 9/2011 | Smith |
| 2011/0238010 A1 | 9/2011 | Kirschenman et al. |
| 2011/0248987 A1 | 10/2011 | Mitchell |
| 2011/0276058 A1 | 11/2011 | Choi et al. |
| 2011/0306873 A1 | 12/2011 | Shenai et al. |
| 2012/0059392 A1 | 3/2012 | Diolaiti |
| 2012/0071752 A1 | 3/2012 | Sewell |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0158011 A1 | 6/2012 | Sandhu |
| 2012/0203067 A1 | 8/2012 | Higgins et al. |
| 2012/0253276 A1 | 10/2012 | Govari et al. |
| 2012/0296161 A1 | 11/2012 | Wallace et al. |
| 2012/0314022 A1 | 12/2012 | Jo |
| 2013/0018306 A1 | 1/2013 | Ludwin |
| 2013/0060146 A1 | 3/2013 | Yang et al. |
| 2013/0165854 A1 | 6/2013 | Sandhu et al. |
| 2013/0317519 A1 | 11/2013 | Romo et al. |
| 2014/0111457 A1 | 4/2014 | Briden et al. |
| 2014/0142591 A1 | 5/2014 | Alvarez et al. |
| 2014/0222204 A1 | 8/2014 | Kawashima |
| 2014/0276392 A1 | 9/2014 | Wong et al. |
| 2014/0276938 A1 | 9/2014 | Hsu et al. |
| 2014/0277333 A1 | 9/2014 | Lewis et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0018622 A1 | 1/2015 | Tesar et al. |
| 2015/0051592 A1 | 2/2015 | Kintz |
| 2015/0105747 A1 | 4/2015 | Rollins et al. |
| 2015/0119638 A1 | 4/2015 | Yu et al. |
| 2015/0157191 A1 | 6/2015 | Phee et al. |
| 2015/0164594 A1 | 6/2015 | Romo et al. |
| 2015/0164596 A1 | 6/2015 | Romo |
| 2015/0224845 A1 | 8/2015 | Anderson et al. |
| 2015/0265807 A1 | 9/2015 | Park et al. |
| 2015/0290454 A1 | 10/2015 | Tyler et al. |
| 2015/0335480 A1 | 11/2015 | Alvarez et al. |
| 2015/0375399 A1 | 12/2015 | Chiu et al. |
| 2016/0001038 A1 | 1/2016 | Romo et al. |
| 2016/0026253 A1 | 1/2016 | Bradski et al. |
| 2016/0059412 A1 | 3/2016 | Oleynik |
| 2016/0098095 A1 | 4/2016 | Gonzalez-Banos et al. |
| 2016/0175059 A1 | 6/2016 | Walker et al. |
| 2016/0183841 A1 | 6/2016 | Duindam et al. |
| 2016/0213436 A1 | 7/2016 | Inoue |
| 2016/0213884 A1 | 7/2016 | Park |
| 2016/0256069 A1* | 9/2016 | Jenkins ............... A61B 90/37 |
| 2016/0270865 A1 | 9/2016 | Landey et al. |
| 2016/0287279 A1 | 10/2016 | Bovay et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1* | 11/2016 | Esterberg ............ A61B 34/10 |
| 2016/0374541 A1 | 12/2016 | Agrawal et al. |
| 2017/0007337 A1 | 1/2017 | Dan |
| 2017/0084027 A1* | 3/2017 | Mintz ................. G06T 7/149 |
| 2017/0100199 A1 | 4/2017 | Yu et al. |
| 2017/0113019 A1 | 4/2017 | Wong et al. |
| 2017/0119413 A1 | 5/2017 | Romo |
| 2017/0119481 A1 | 5/2017 | Romo et al. |
| 2017/0143429 A1 | 5/2017 | Richmond et al. |
| 2017/0165011 A1 | 6/2017 | Bovay et al. |
| 2017/0172664 A1 | 6/2017 | Weingarten et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1* | 12/2017 | Mintz ................. G06T 7/248 |
| 2017/0367782 A1 | 12/2017 | Schuh et al. |
| 2018/0025666 A1 | 1/2018 | Ho et al. |
| 2018/0078321 A1 | 3/2018 | Liao |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0090969 A1 | 3/2019 | Jarc et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151032 A1 | 5/2019 | Mustufa et al. |
| 2019/0151148 A1 | 5/2019 | Alvarez et al. |
| 2019/0167361 A1 | 6/2019 | Walker et al. |
| 2019/0167366 A1 | 6/2019 | Ummalaneni |
| 2019/0175009 A1 | 6/2019 | Mintz |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0371012 A1* | 12/2019 | Flexman ............. G06T 11/00 |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |

(56) References Cited

U.S. PATENT DOCUMENTS

| | | |
|---|---|---|
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0101264 A1 | 4/2020 | Jiang |
| 2020/0107894 A1 | 4/2020 | Wallace |
| 2020/0121502 A1 | 4/2020 | Kintz |

FOREIGN PATENT DOCUMENTS

| | | |
|---|---|---|
| WO | WO 08/049088 | 4/2008 |
| WO | WO 10/025522 | 3/2010 |

* cited by examiner

SYSTEM AND METHOD FOR MEDICAL INSTRUMENT NAVIGATION AND TARGETING

CROSS-REFERENCE TO RELATED APPLICATION(S)

This application claims the benefit of U.S. Provisional Application No. 62/596,710, filed Dec. 8, 2017, which is hereby incorporated by reference in its entirety.

TECHNICAL FIELD

The systems and methods disclosed herein are directed to medical instrument navigation and targeting, and more particularly to techniques for assisting in targeting a region within a luminal network during medical instrument navigation.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the medical tool during a medical procedure. The surgical robotic system may comprise at least one robotic arm including a manipulator assembly which may be used to control the positioning of the medical tool prior to and during the medical procedure. Certain medical procedures (e.g., a biopsy procedure) may involve positioning a distal end of the medical tool adjacent to a target (such as a target nodule) within the luminal network. It may be desirable to incorporate feedback mechanisms that provide position and/or orientation information of the medical tool with respect to the target to aid in maneuvering the medical tool during the procedure.

SUMMARY

The systems, methods and devices of this disclosure each have several innovative aspects, no single one of which is solely responsible for the desirable attributes disclosed herein.

In one aspect, there is provided a system comprising a medical instrument having an elongate body and at least one sensor; a display; a processor; and a memory storing a model of a mapped portion of a luminal network and a position of a target with respect to the model, the memory further storing computer-executable instructions to cause the processor to: determine, based on data from the at least one sensor, a position and orientation of a distal end of the medical instrument with respect to the model, and cause, on at least a portion of the display, a rendering of the model, the position of the target, and the position and orientation of the distal end of the medical instrument, wherein the rendering is based on a viewpoint directed at the target and different from a viewpoint of the medical instrument.

In another aspect, there is provided a non-transitory computer readable storage medium having stored thereon instructions that, when executed, cause at least one computing device to: determine, based on data from at least one sensor of a medical instrument, a position and orientation of a distal end of the medical instrument with respect to a model of a mapped portion of a luminal network, and cause, on at least a portion of a display, a rendering of the model, a position of a target with respect to the model, and the position and orientation of the distal end of the medical instrument, wherein the rendering is based on a viewpoint directed at the target and different from a viewpoint of the medical instrument.

In yet another aspect, there is provided a method of navigating a medical instrument, comprising: determining, based on data from at least one sensor of the medical instrument, a position and orientation of a distal end of the medical instrument with respect to a model of a mapped portion of a luminal network, and causing, on at least a portion of a display, a rendering of the model, a position of a target with respect to the model, and the position and orientation of the distal end of the medical instrument, wherein the rendering is based on a viewpoint directed at the target and different from a viewpoint of the medical instrument.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
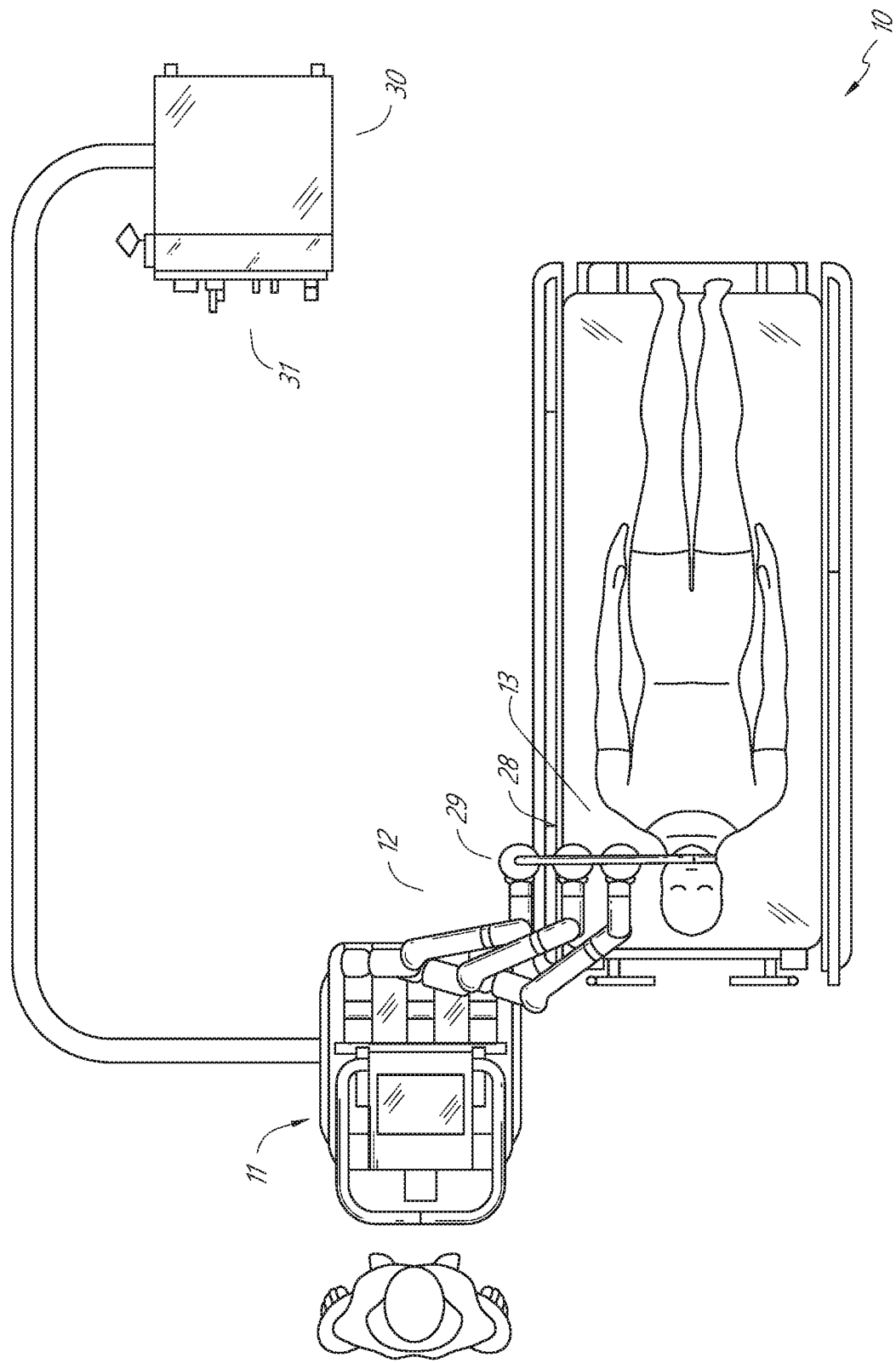
FIG. 1 illustrates an embodiment of a cart-based robotic system arranged for diagnostic and/or therapeutic bronchoscopy procedure(s).
Figure 2:
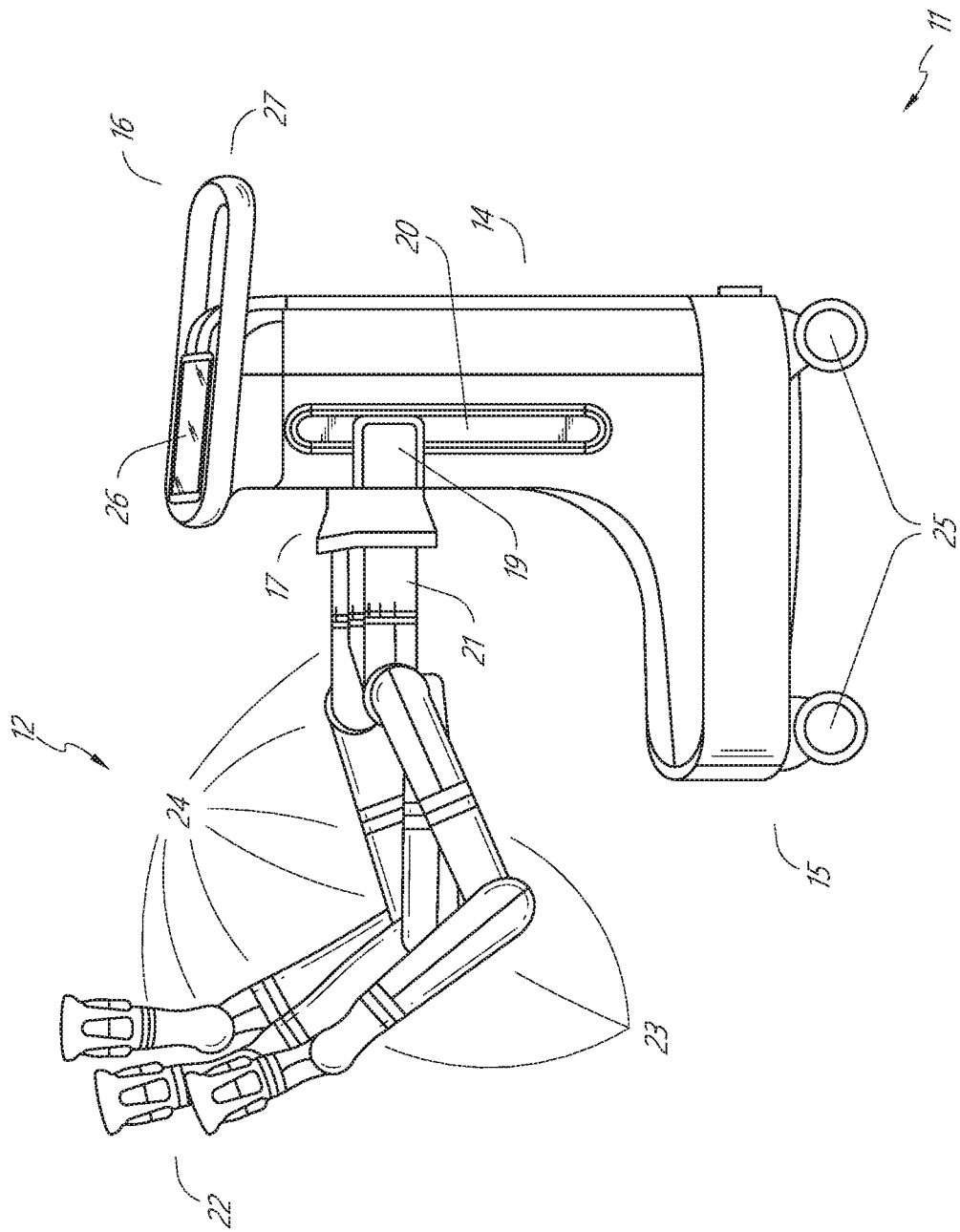
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
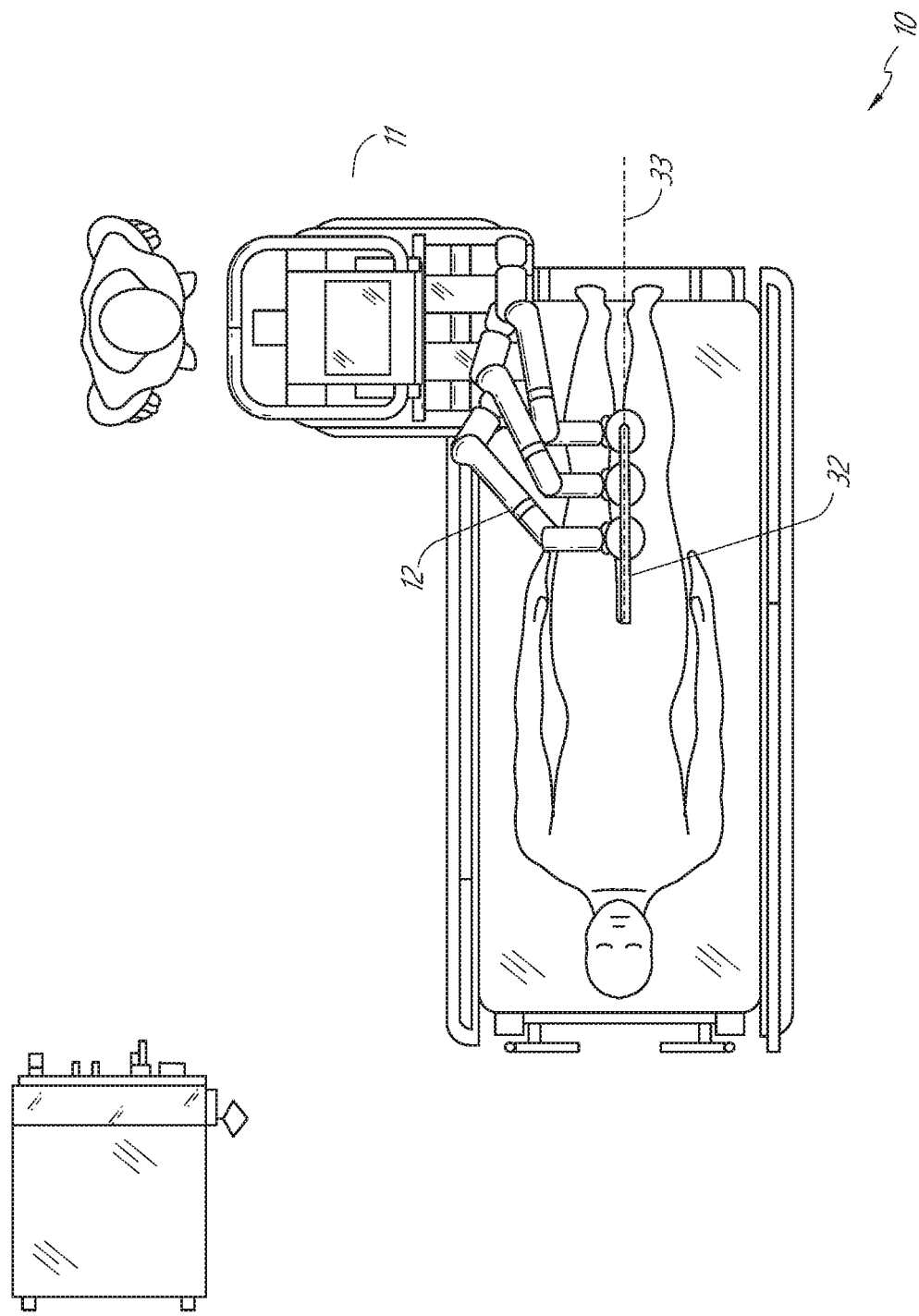
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
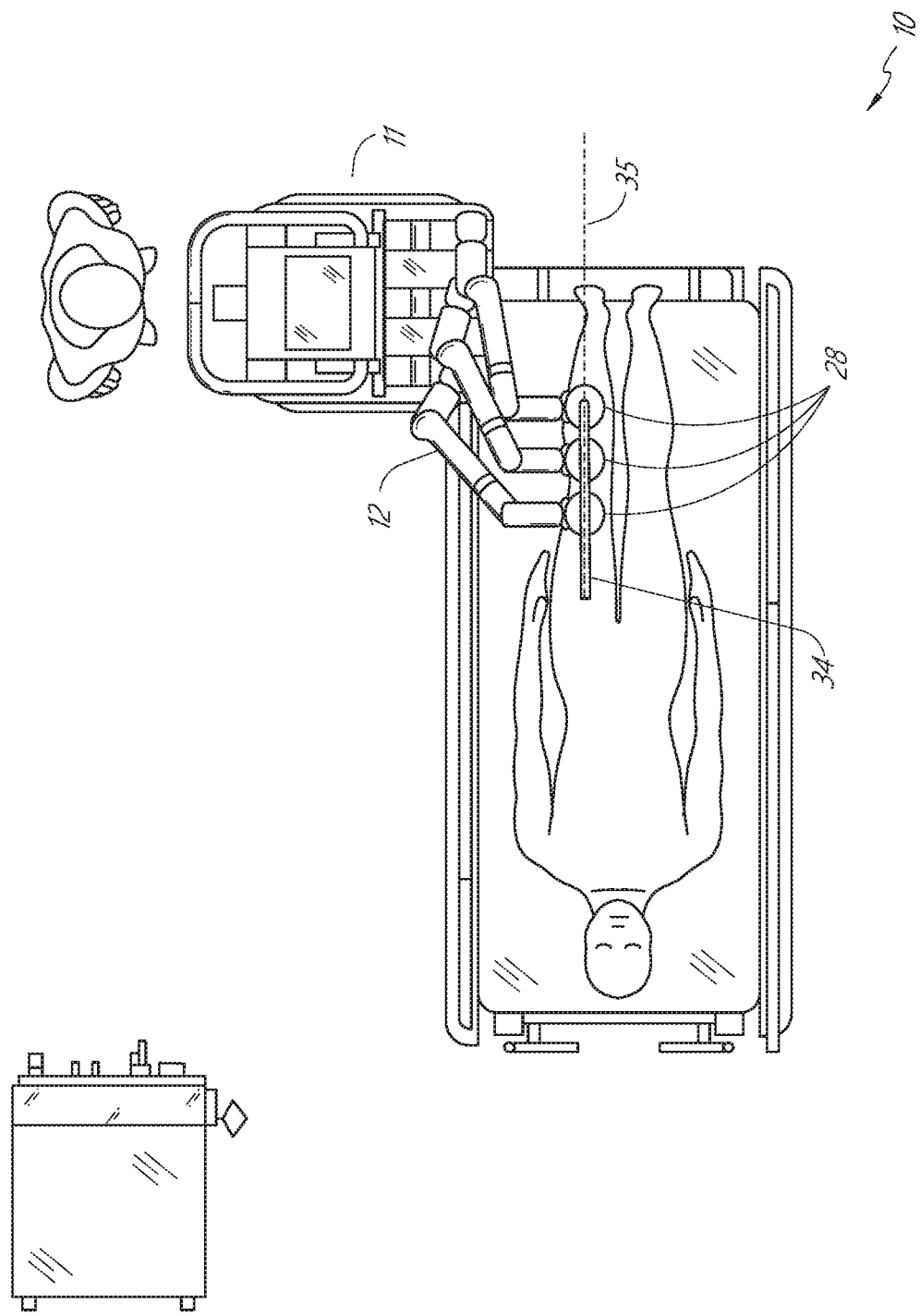
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
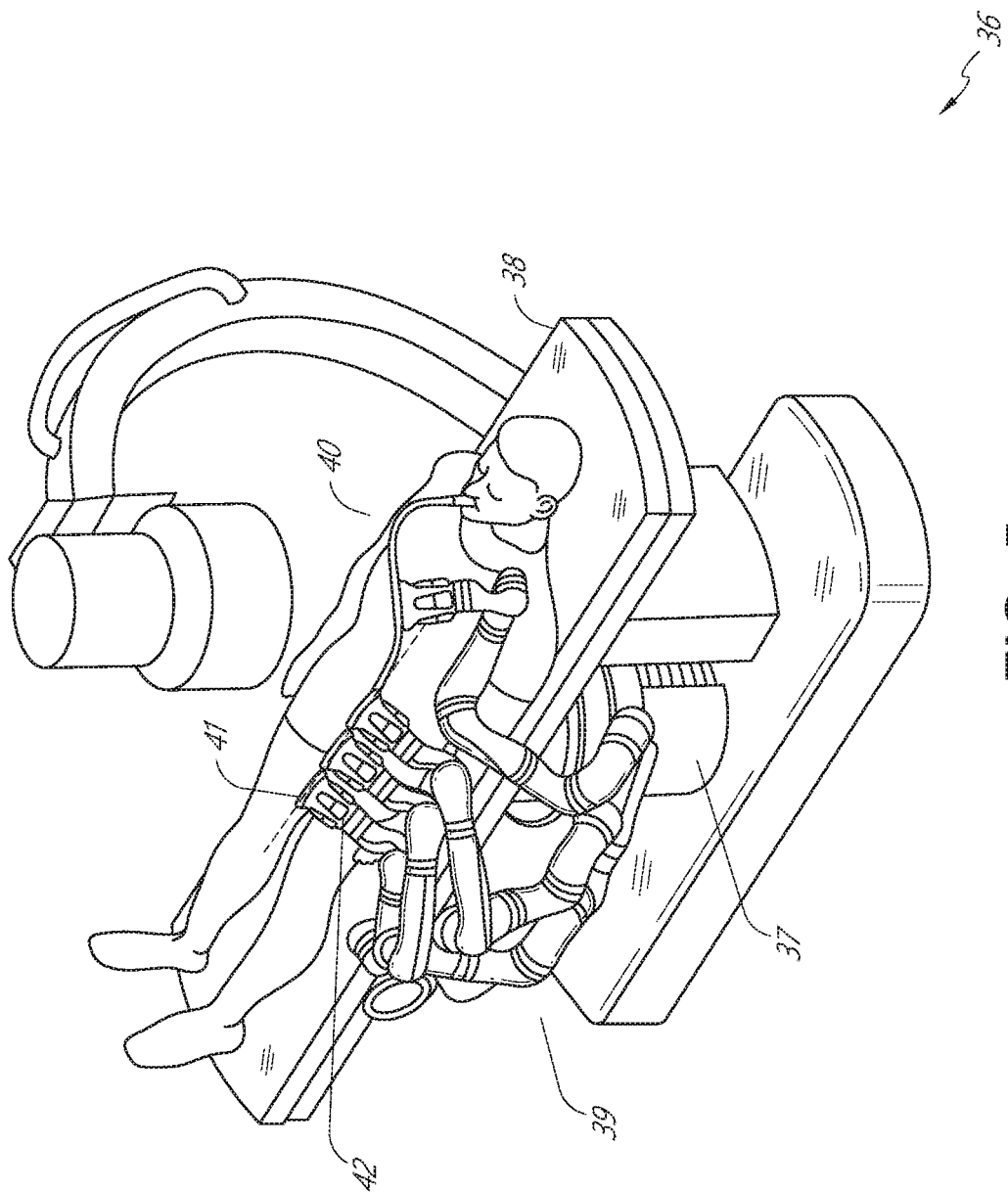
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
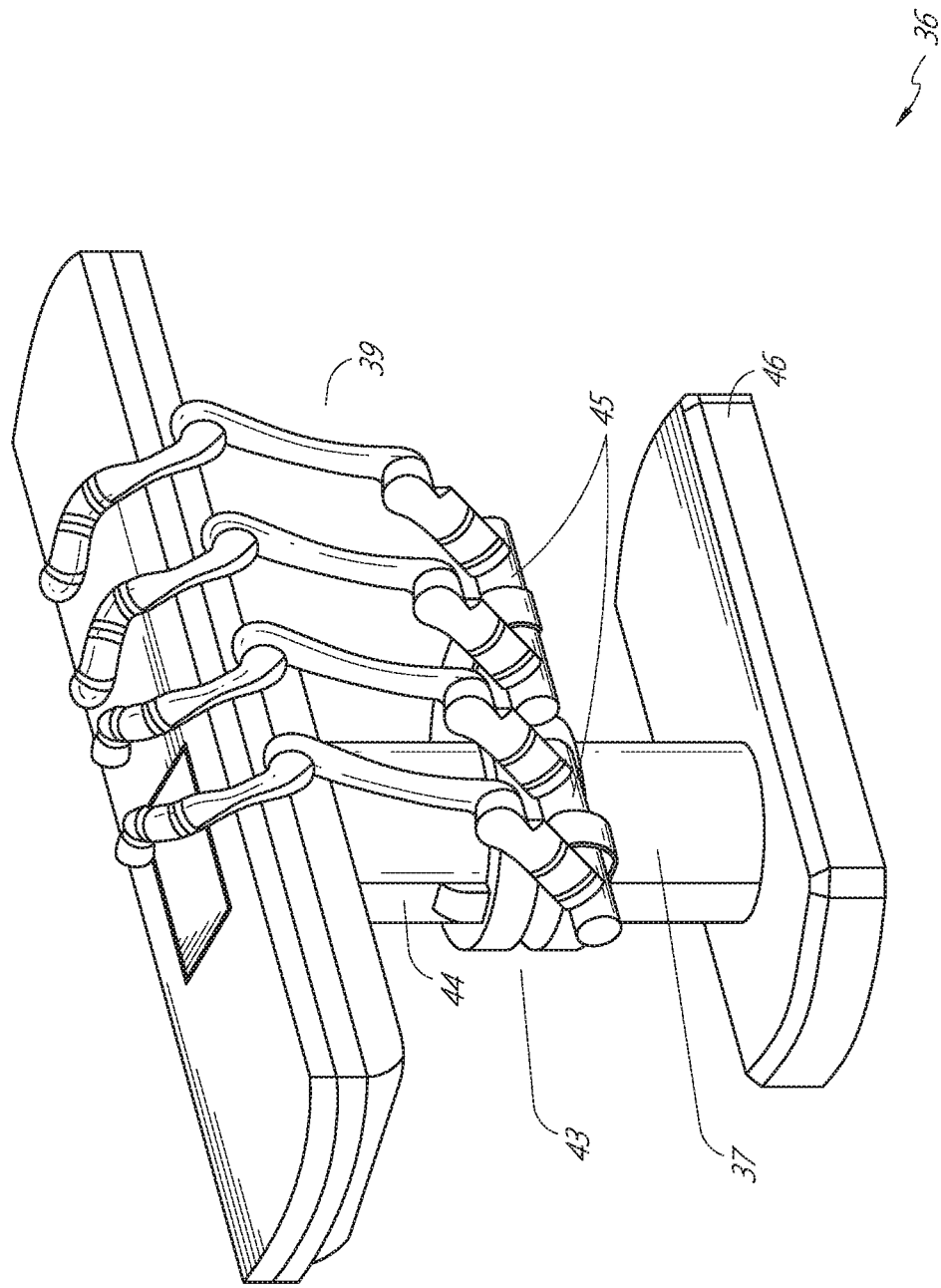
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
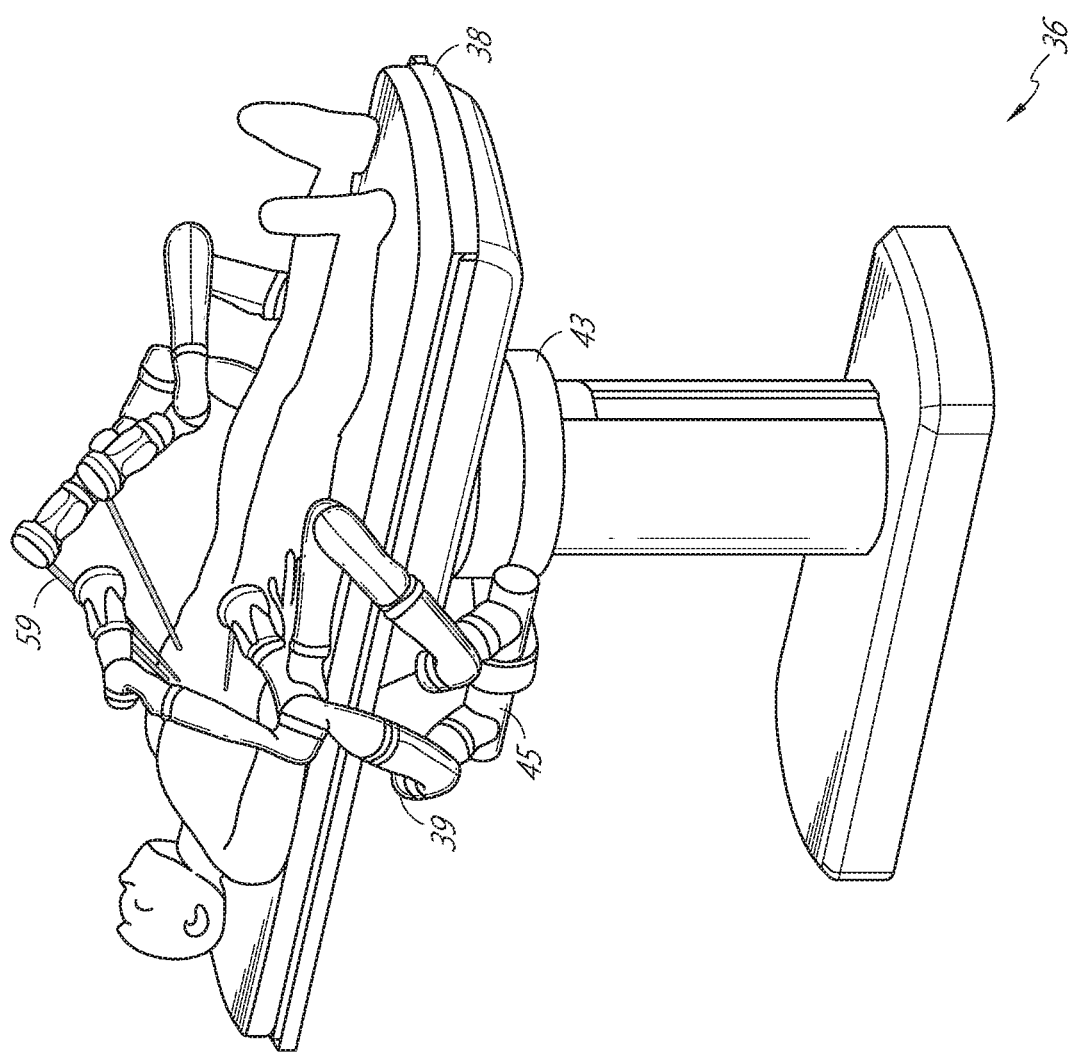
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
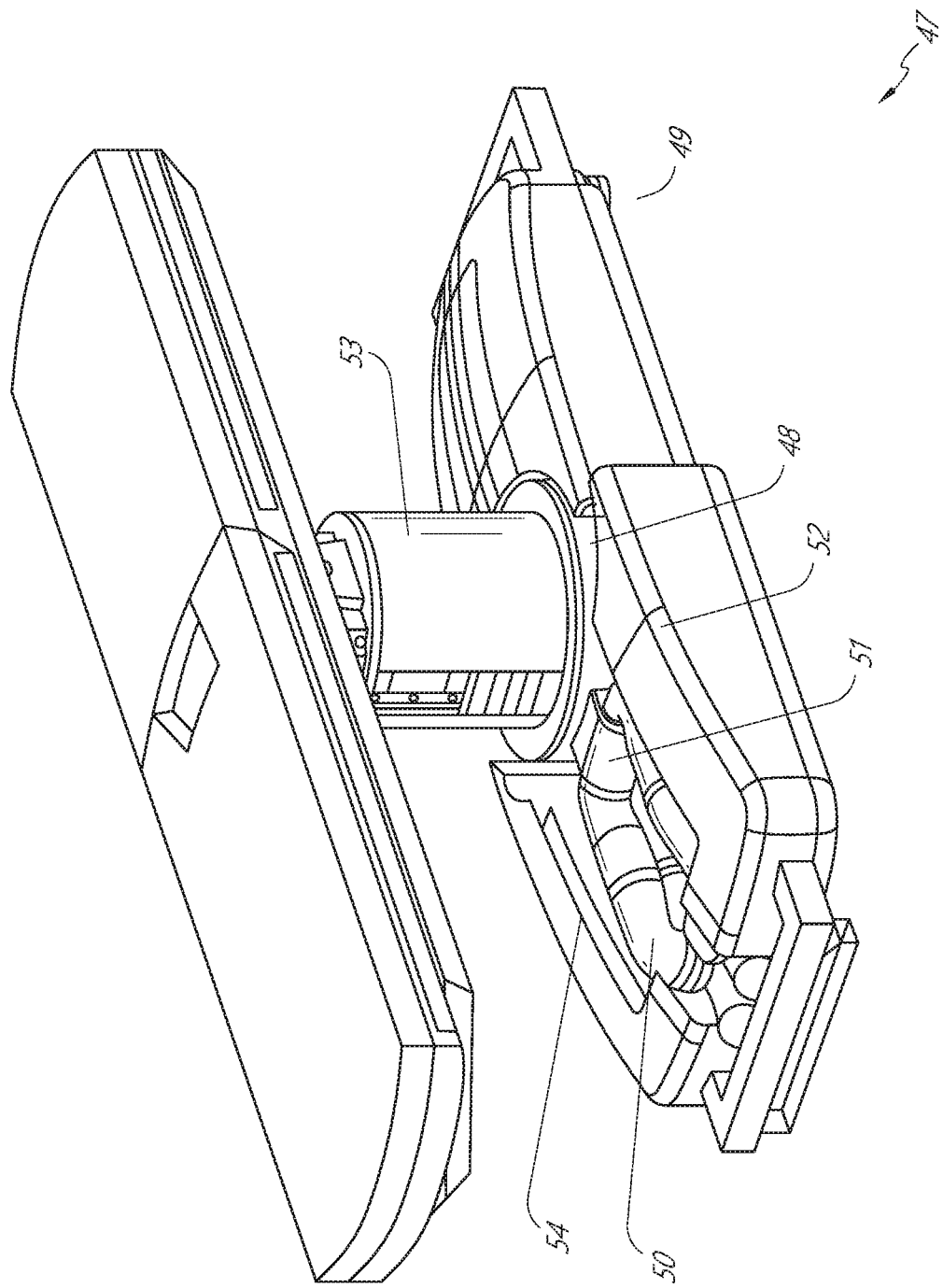
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
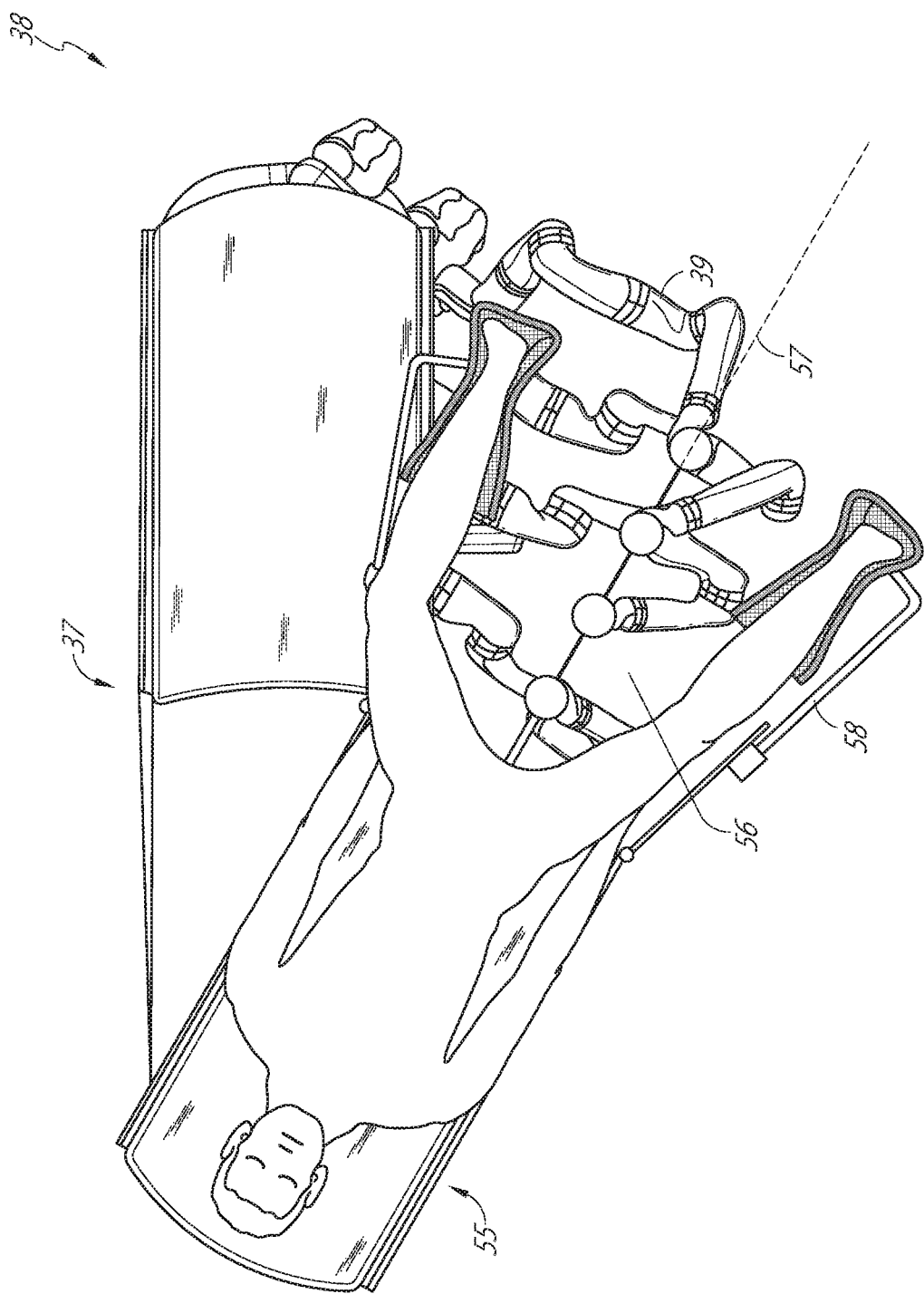
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
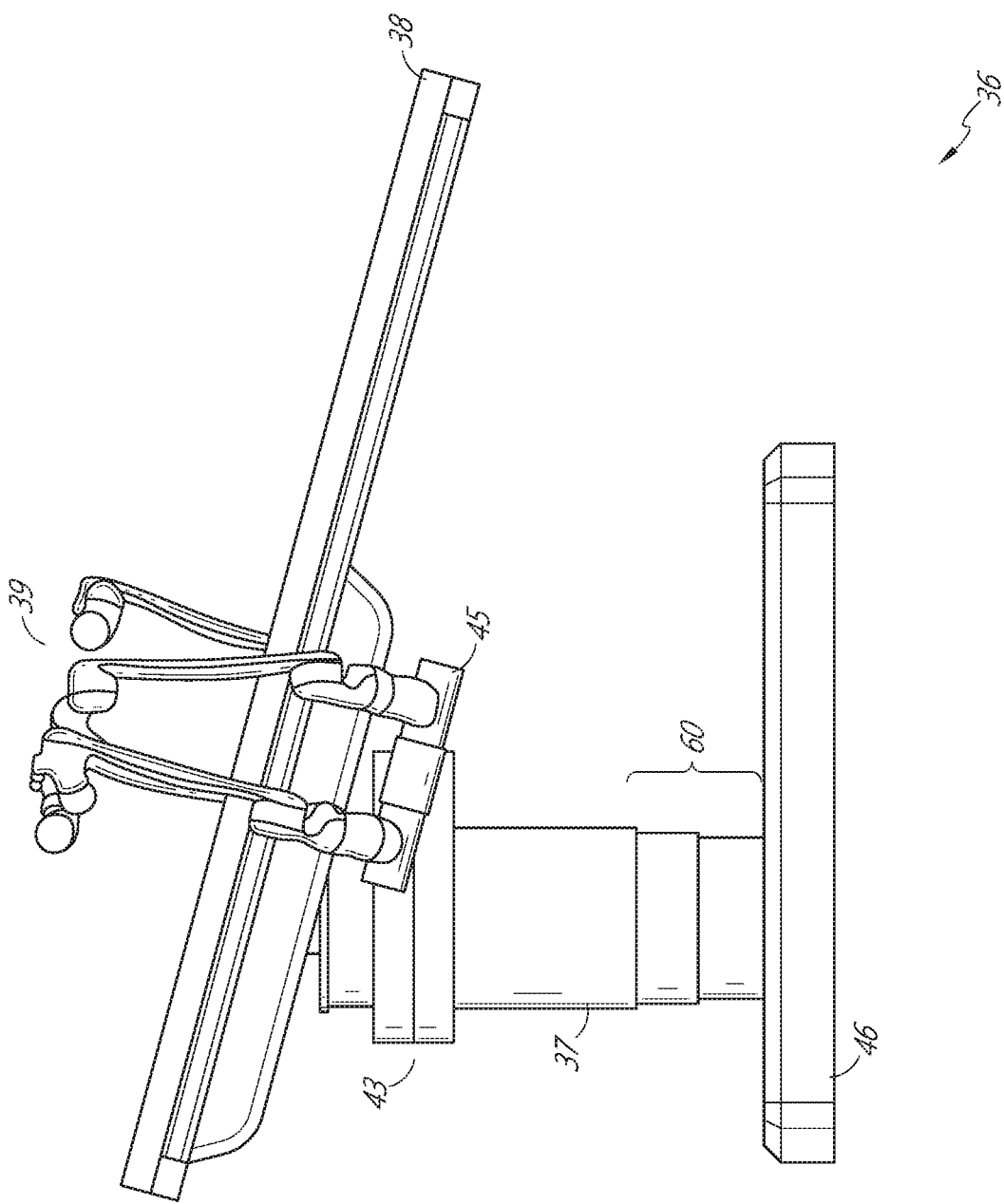
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
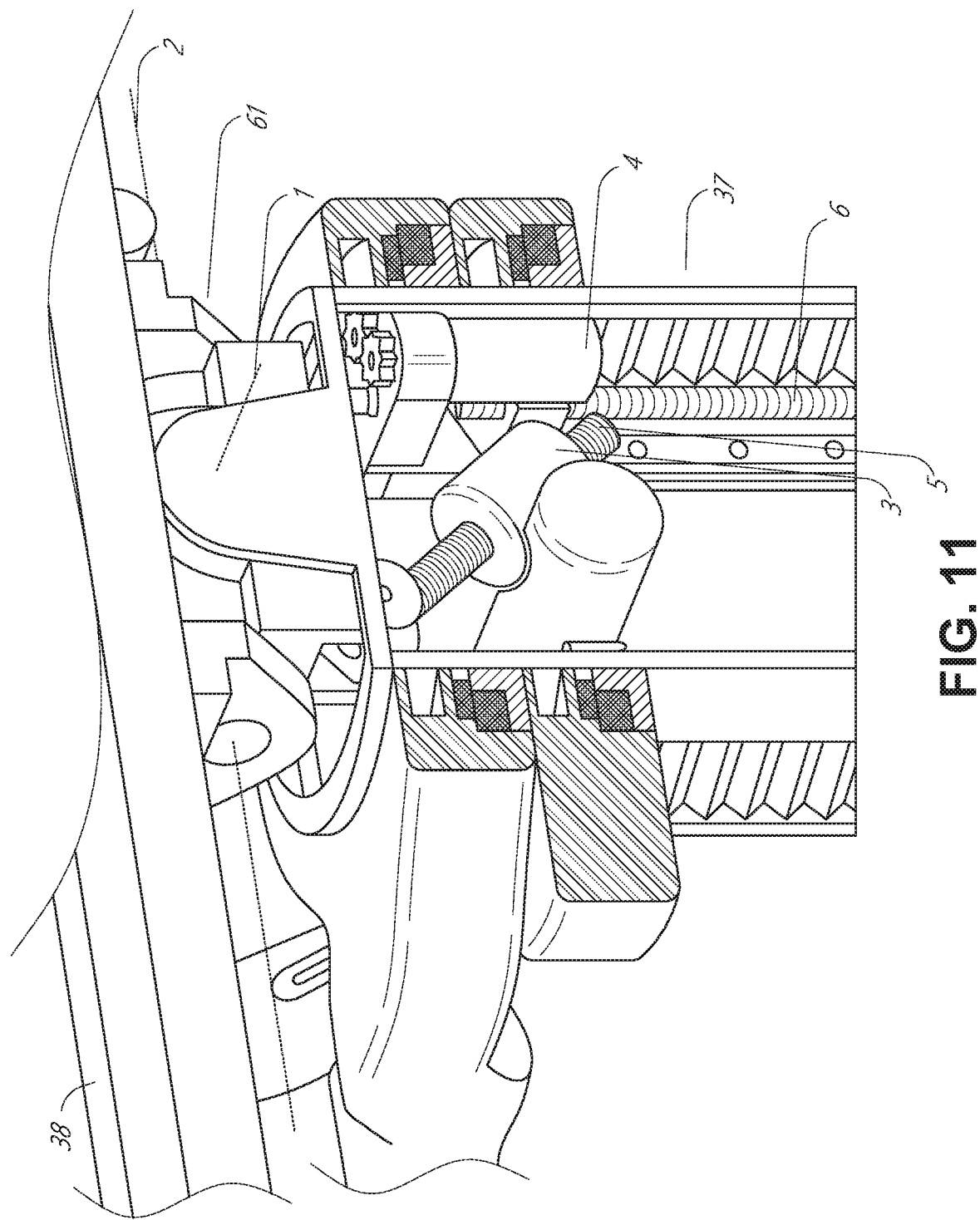
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
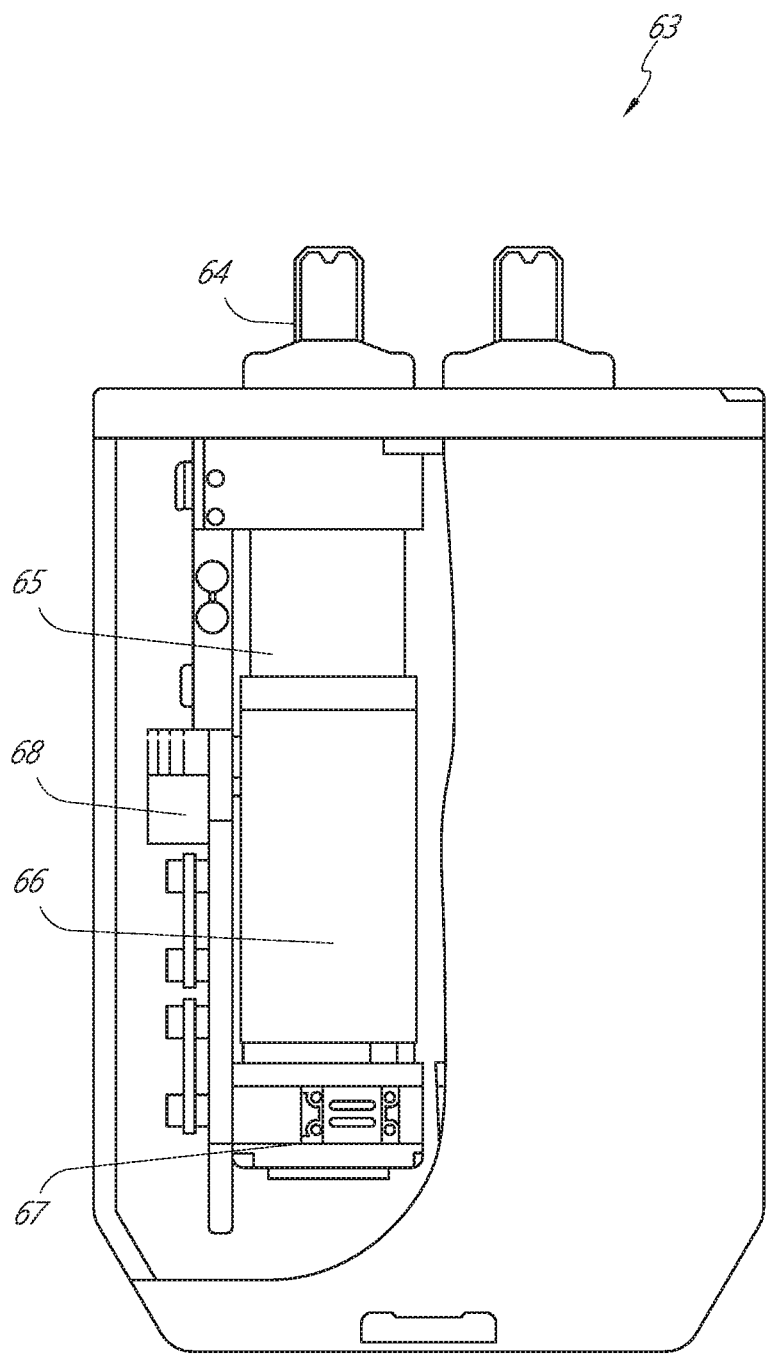
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
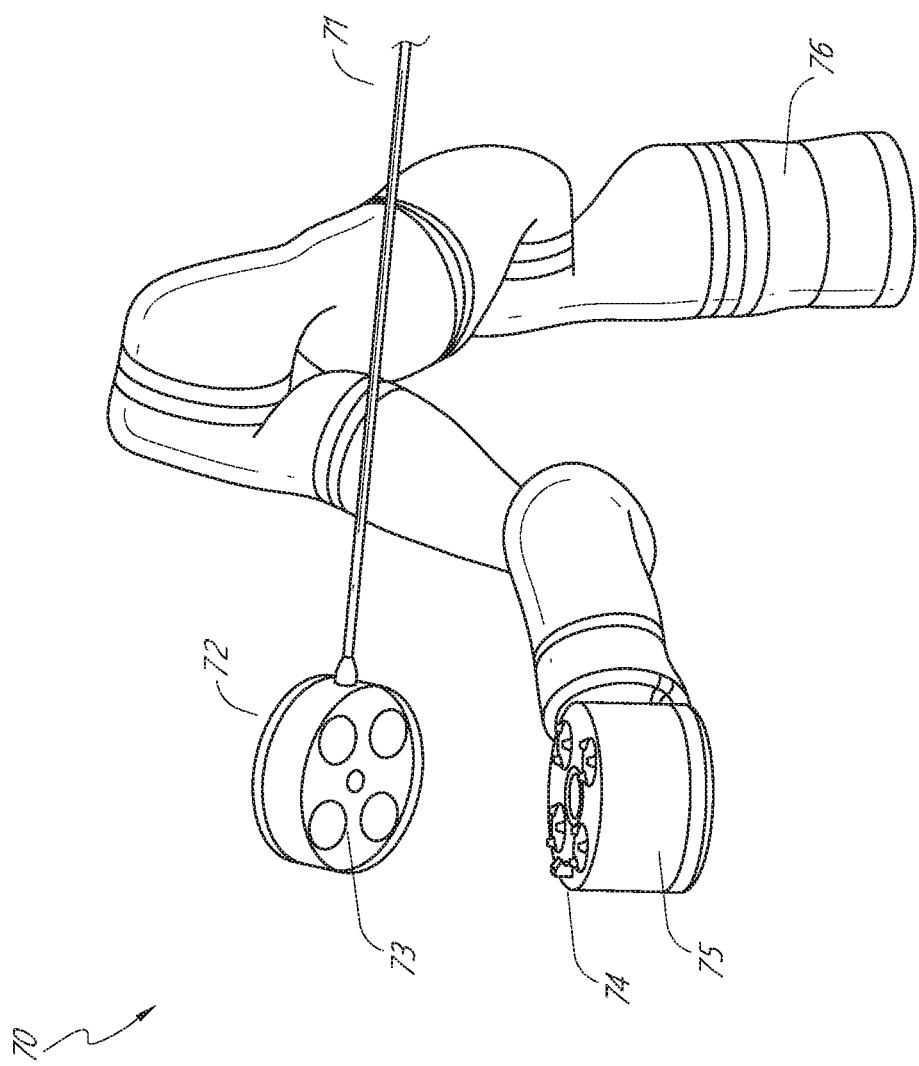
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
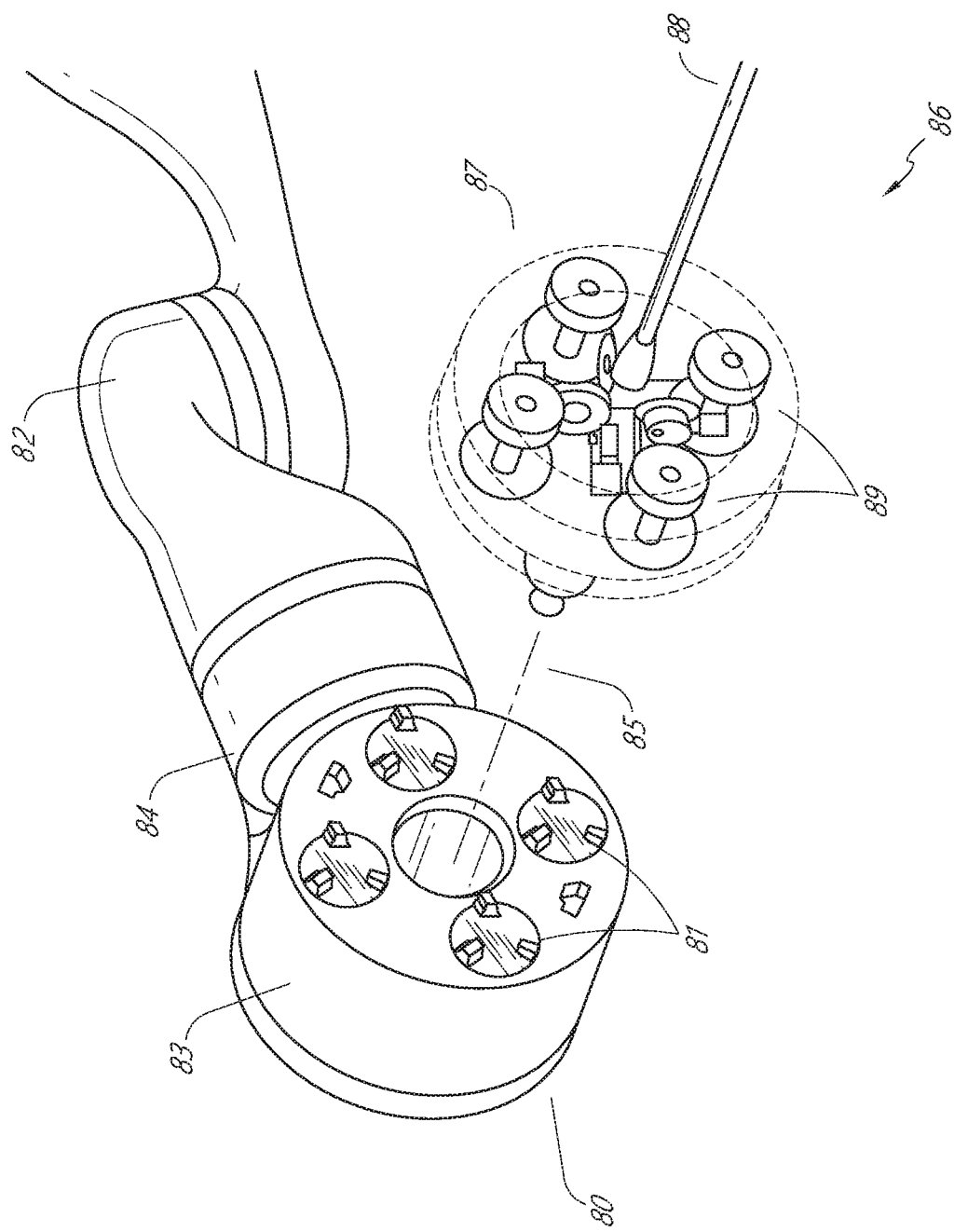
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
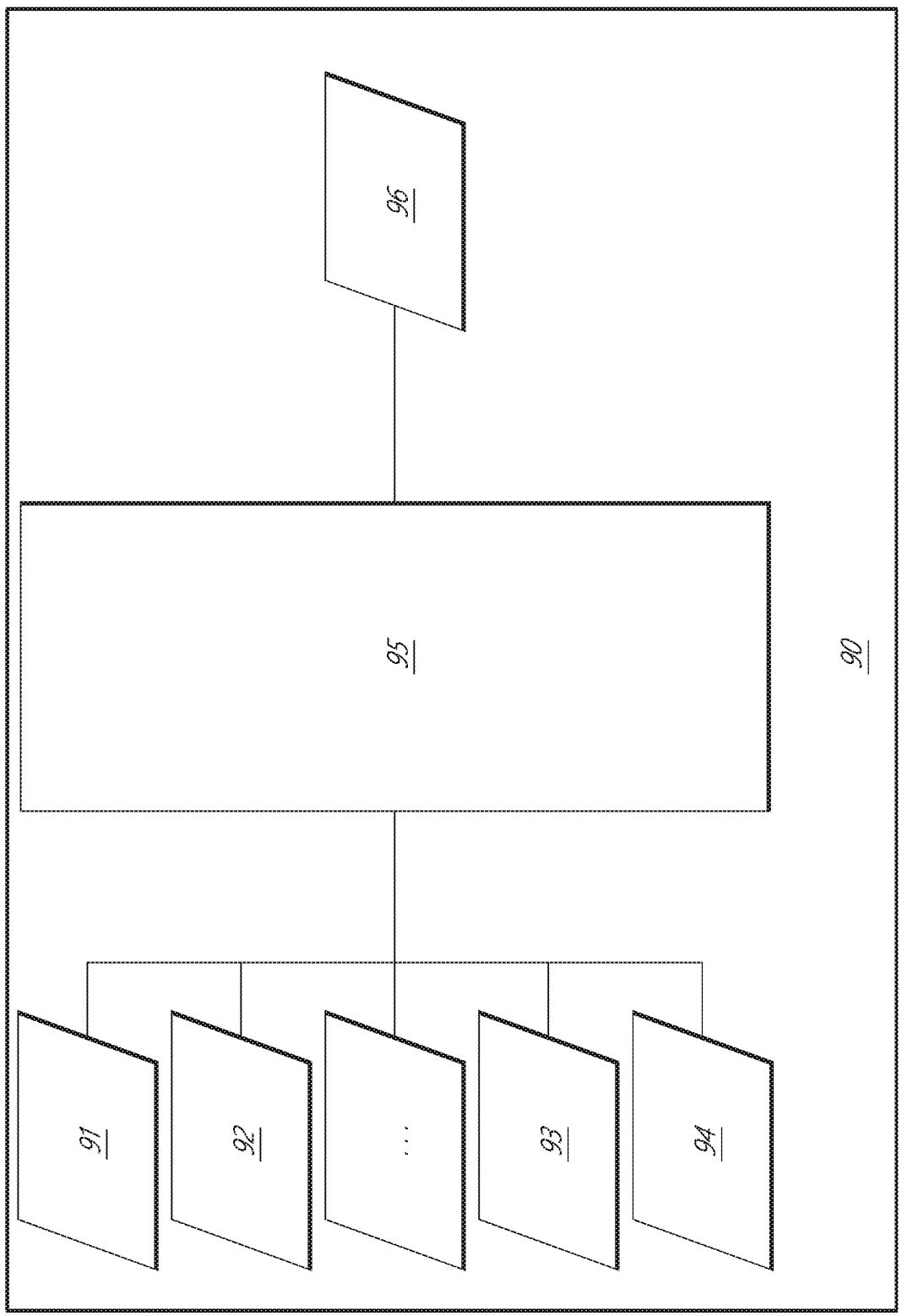
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 (also referred to as a "state fusion module") that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Targeting During Navigation.

Embodiments of this disclosure relate to systems and techniques for targeting a specific region within a luminal network during navigation of a medical instrument. Certain medical procedures may involve driving a medical instrument to a predetermined location adjacent to a target region (also simply referred to as a "target" herein). For example, preoperative imaging of a patient may reveal an area of interest (e.g., a nodule, lesion, etc.) for diagnosis and/or treatment. In one implementation, the medical procedure may involve navigating the medical instrument to within a threshold working distance from a target nodule and taking a biopsy of the target nodule. However, the targeting methods and techniques described herein are not limited to biopsy procedures and may be applicable to any medical procedure involving the navigation of a medical instrument to a target.

In certain embodiments, as a medical instrument is navigated through a luminal network, the position of the instrument may be determined and visual indicia indicative of the position of the instrument may be displayed (e.g., plotted or otherwise displayed) to provide visual feedback. The visual indicia can also be used to visualize the shape of the luminal network with respect to a target and/or the medical instrument.

A. Example Luminal Networks and Models.

Figure 16:
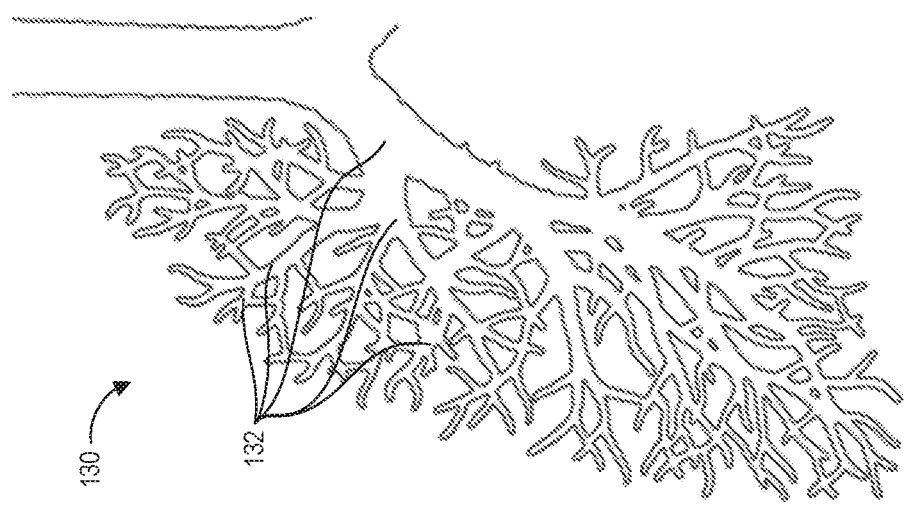
FIG. 16 illustrates an example luminal network that can be navigated by a robotically controlled medical instrument.

FIG. 16 illustrates an example luminal network 130 of a patient that can be navigated using the methods and systems described herein. In the illustrated embodiment, the luminal network 130 is a bronchial network of airways inside a patient's lung. As illustrated, the luminal network 130 comprises a plurality of lumens 132 that are arranged in a branched structure. Although the illustrated luminal network 130 comprises a plurality of branched lumens 132, in some instances, the luminal network 130 may comprise only a single lumen 132. That is, in some instances, a luminal network 130 need not comprise a branched arrangement of lumens 132. For ease of illustration, FIG. 16 represents the luminal network 130 as a two-dimensional structure. This should not be construed to limit the present disclosure to two-dimensional luminal networks in any way. In general, the luminal network 130 comprises a three-dimensional structure.

Although a particular luminal network 130 is illustrated in FIG. 16, the instrument navigation and targeting methods and systems described herein can be implemented during navigation of a wide variety of luminal networks 130. Such luminal network 130 can include, for example, bronchial networks, renal networks, cardiovascular networks (e.g., arteries and veins), gastrointestinal tracts, urinary tracts, etc. The instrument navigation and targeting methods and systems described herein can be implemented during navigation of both branched and non-branched luminal networks 130.

Figure 17:
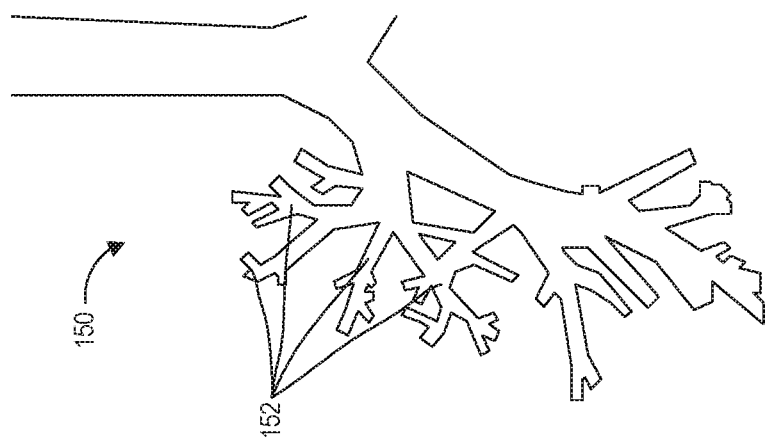
FIG. 17 illustrates an example model of the luminal network of FIG. 16.

FIG. 17 illustrates an example model 150 of the luminal network 130 of FIG. 16. In certain implementations, the model 150 may be constructed from preoperative imaging of the luminal network 130. However, in other implementations, the model 150 may be generated using intraoperative images taken during a medical procedure or may be constructed using preoperative images in addition to intraoperative images. As will be described in greater detail below, in some instances, the model may be used to facilitate navigation of a medical instrument through the luminal network 130. In some instances, the model 150 may be displayed to a user prior to and/or during navigation of the luminal network 130.

The model 150 may be representative of one or more portions of the luminal network 130 that is being navigated by the medical instrument. In some implementations, the model 150 may be generated prior to navigation of the luminal network using one or more of various preoperative imaging and mapping techniques. For example, preoperative mapping may be accomplished through the use of a collection of low dose computer tomography (CT) scans. As discussed above, preoperative CT scans can generate two-dimensional images, each representing a "slice" of a cut-away view of the patient's internal anatomy. When analyzed in the aggregate, image-based models for anatomical cavities, spaces, and structures of the patient's anatomy, such as a patient lung network (i.e., a luminal network), may be generated. Other methods for generating the model 150, including the use of intraoperative CT scans, are also possible.

In the illustrated embodiment, the model 150 comprises a plurality of segments 152. The segments 152 of the model 150 correspond with at least a portion of the lumens 132 of the luminal network 130. Thus, if the luminal network 130 comprises a branched arrangement of lumens 132, the model 150 may comprise a corresponding branched arrangement of segments 152. If the luminal network 130 comprises a single lumen 132, the model 150 can comprise a corresponding single branch 152. In general, the model 150 comprises a three-dimensional shape, corresponding to at least a portion of the three-dimensional shape of the luminal network 130. Although the model 150 may comprise a three-dimensional shape, FIG. 17 illustrates the model 150 as a two-dimensional shape for ease of illustration. In some instances, a cross-section of a three-dimensional model 150 may be displayed on a two-dimensional display.

Comparing the luminal network 130 of FIG. 16 and the model 150 of FIG. 17, it can be seen that, in some instances, the model 150 may represent or correspond to only a portion of the luminal network 130. This is further illustrated in FIG. 18, which is a view of the model 150 overlaid on the luminal network 130. In some instances, limitations in the imaging and mapping techniques used to generate the model 150 may prevent generation of a model that corresponds to the entire luminal network 130. For example, certain branched lumens 132 within the luminal network may be sufficiently small that they cannot be clearly depicted and analyzed with common imaging and mapping techniques. As such, the model 150 may not provide a complete representation of the luminal network 130, for example, leaving various portions of the luminal network 130 unmapped and/or unrepresented in the model 150.

Figure 18:
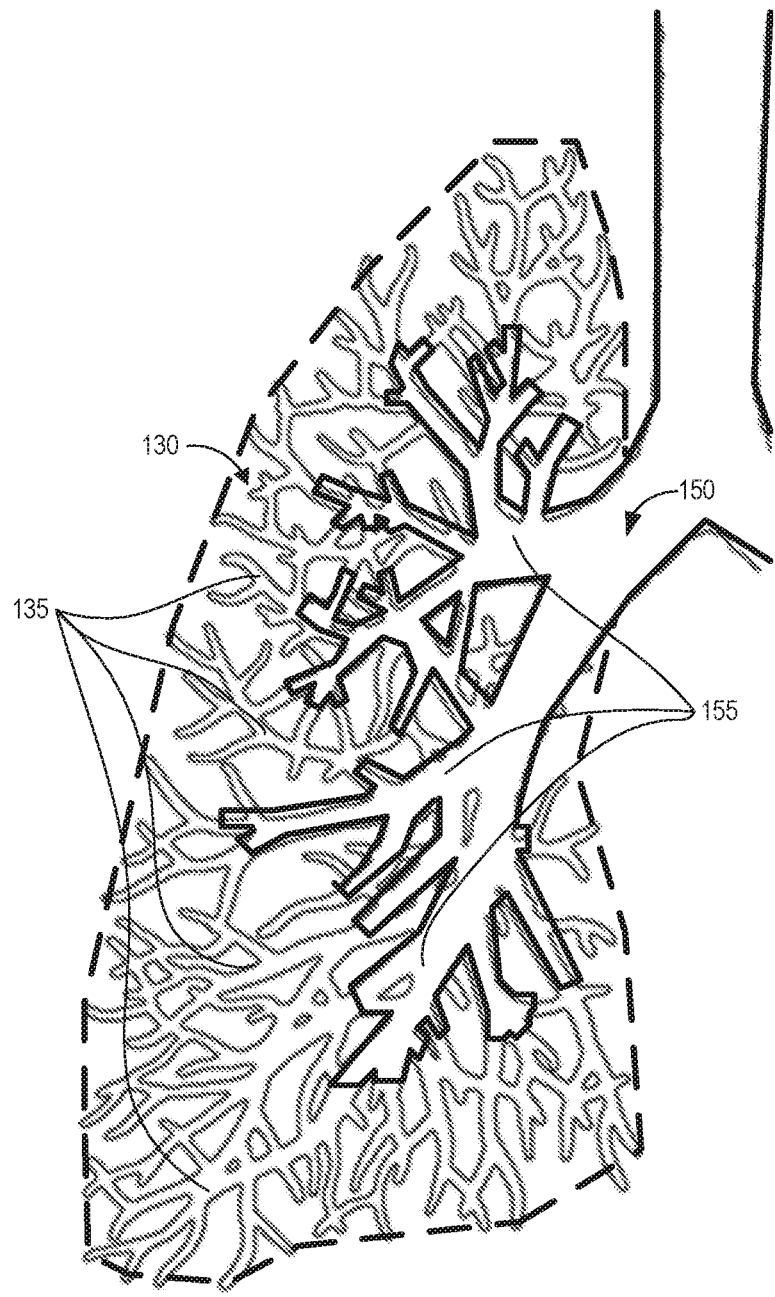
FIG. 18 is a view of the model of FIG. 17 overlaid on the luminal network of FIG. 16 wherein the model corresponds to a mapped portion of the luminal network.

For example, as shown in FIG. 18, the model 150 can correspond to a mapped portion 155 of the luminal network 130. An unmapped portion 135 of the luminal network 130, which may not represented by the model 150, may extend beyond the mapped portion 155.

In some embodiments, the model 150 may also include a representation of an outer surface of the organ that includes the luminal network. For example, in the case of the a lung, a model may include a representation of at least a portion of the airways and also an exterior surface of the lung.

B. Navigation of a Luminal Network with a Medical Instrument.

Figure 19:
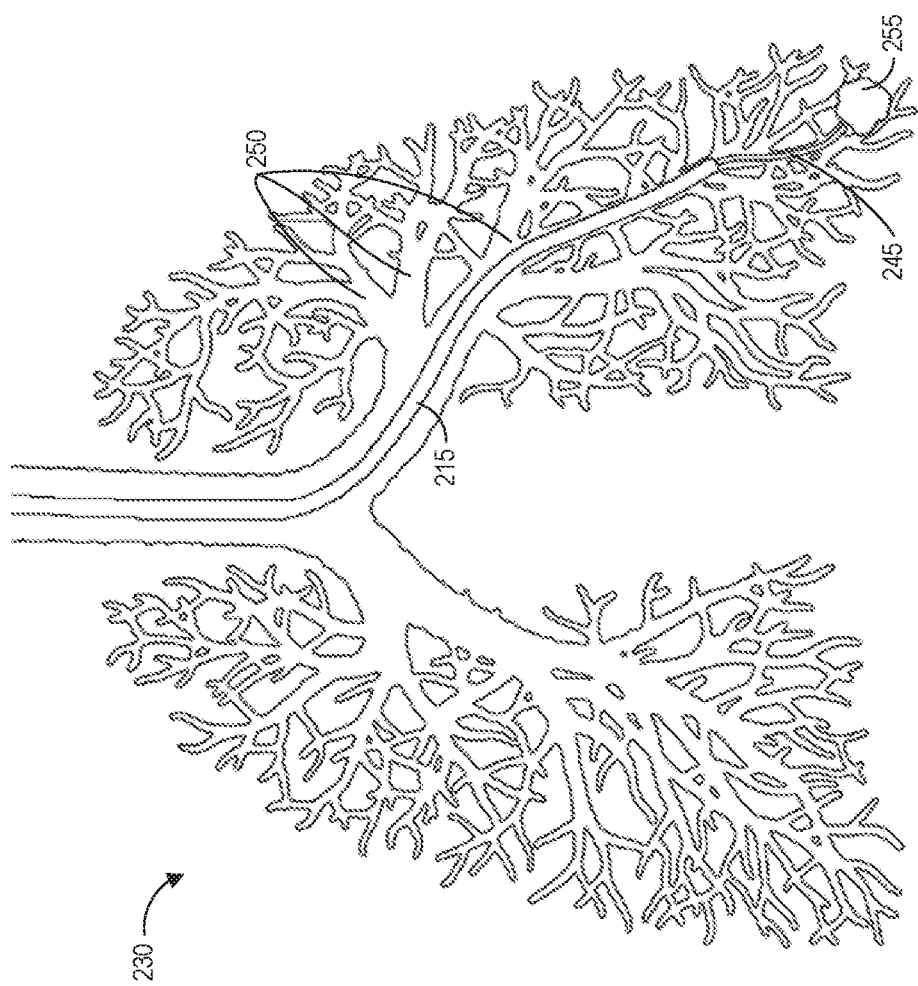
FIG. 19 provides an example of a medical instrument navigating within a luminal network.

FIG. 19 provides an example of a medical instrument, for example, including a sheath 215 and a leader 245, positioned within a luminal network 230. As illustrated, the luminal network 230 (which may be similar to the luminal network 130 described above) includes a branched structure of airways 250 (which may be similar to lumens 132). In this example, the sheath 215 is navigated (e.g., directed, guided, moved, etc.) through the luminal network 230 towards a target (e.g., nodule 255) or area of interest for diagnosis and/or treatment. In the illustrated example, the nodule 255 is located at a periphery of the luminal network 230 and airways 250. The sheath 215 has a first diameter and thus its distal end may not be able to be positioned through the smaller-diameter airways around the nodule 255 which may have a diameter less than the first diameter of the sheath 215. Accordingly, the leader 245 can be guided through or placed within a working channel of the sheath 215 and advanced through the remaining distance in the airway 250 to the nodule 255. For example, the leader 245 may comprise an articulating catheter that can be driven through the working channel of the sheath 215 and/or the airway 250. The leader 245 may have a lumen through which instruments, such as biopsy needles, cytology brushes, tissue sampling forceps, etc., can be passed to the target tissue site of nodule 255. In such implementations, both the distal end of the sheath 215 and the distal end of the leader 245 can be provided with EM instrument sensors (and/or other position sensors) for tracking their positions within the airways 250. In other embodiments, the overall diameter of the sheath 215 may be small enough to reach the periphery without the leader 245, or may be small enough to get close to the periphery (e.g., within 2.5-3 cm) to deploy medical instruments, e.g., through a non-steerable leader 245. The medical instruments deployed through the sheath 215 may be equipped with EM instrument sensors (and/or other position sensors).

As mentioned above, in the example of FIG. 19, the nodule 255 is located at the periphery of the luminal network 230. This may be in an area of the luminal network 230 that is not represented by a model (e.g., constructed from pre-operative imaging of the luminal network 230 and/or intra-operative images of the luminal network 230 taken during a medical procedure, which may be analogous to the example model 150 of the luminal network 130 shown in FIGS. 17 and 18). That is, the nodule 255 may, in some instances, be located within the unmapped portion of the luminal network 230 (analogous to the unmapped portion 135 of the luminal network 130 shown in FIG. 18). In other examples, the nodule 255 may be located adjacent to the luminal network 230, and thus, may be positioned outside of the model 150.

Figure 20:
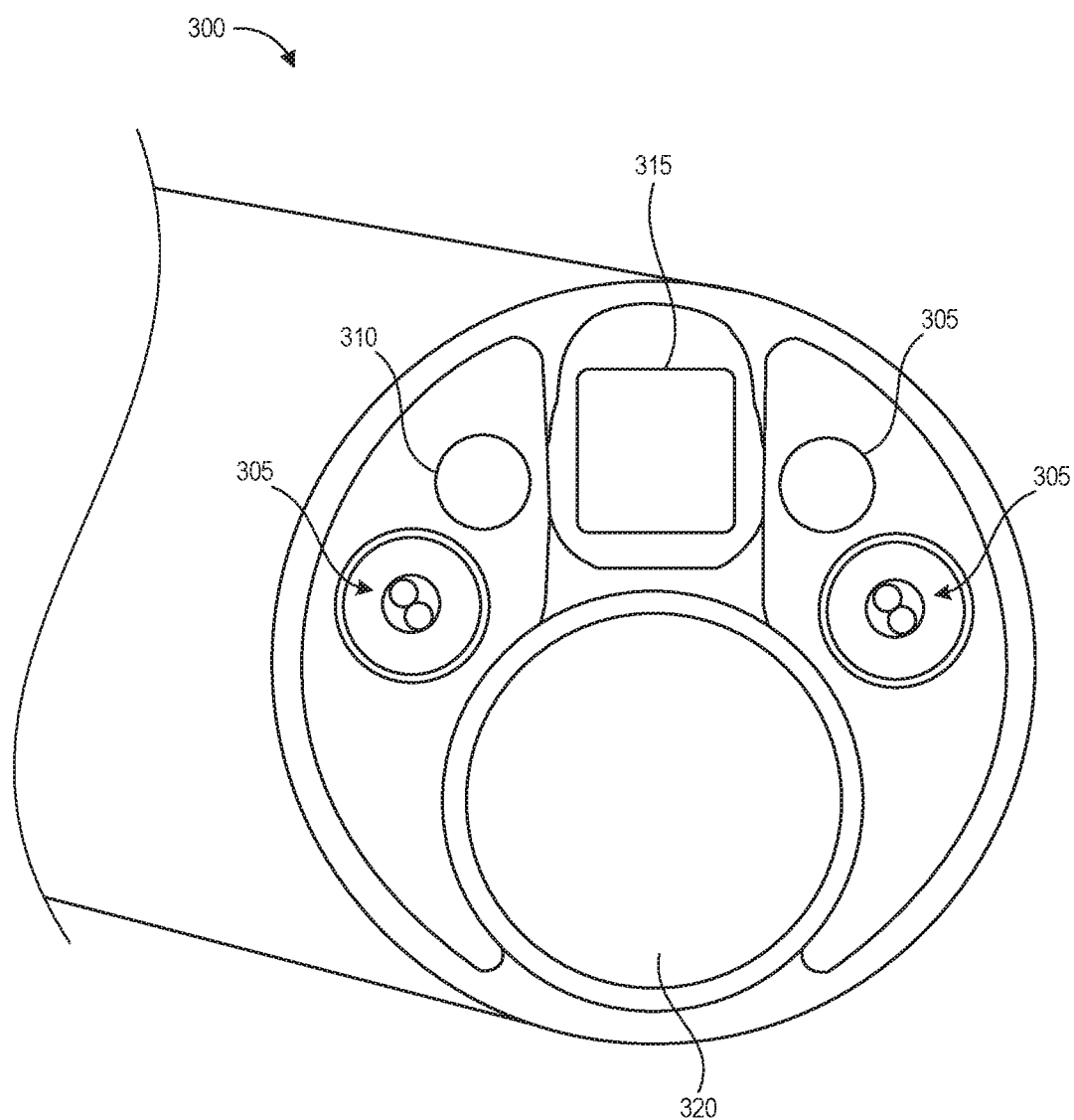
FIG. 20 illustrates a distal end of an example medical instrument.

FIG. 20 provides a detailed view of a distal end of an example medical instrument 300. The medical instrument 300 be representative of the sheath 215 or the leader 245 of FIG. 19. The medical instrument 300 may be representative of any medical instrument described throughout the disclosure, including but not limited to the endoscope 13 of FIG. 1, the ureteroscope 32 of FIG. 3, the laparoscope 59 of FIG. 9, etc. In FIG. 20, the distal end of the instrument 300 includes an imaging device 315, illumination sources 310, and ends of EM sensor coils 305, which form an EM instrument sensor. The distal end further includes an opening to a working channel 320 of the instrument 300 through which surgical (or medical) instruments, such as biopsy needles, cytology brushes, forceps, etc., may be inserted (e.g., at a proximal end of the instrument 300) and advanced along the instrument shaft, allowing access to the area near the distal end or tip of the instrument 300.

EM coils 305 (also referred to as EM position sensors 305) may be positioned on the distal end of the instrument 300 and may be used with an EM tracking system (see, e.g., FIG. 21 described below) to detect the position and orientation of the distal end of the instrument 300 while it is positioned within a luminal network. In some embodiments, the coils 305 may be angled to provide sensitivity to EM fields along different axes, giving the disclosed navigational systems the ability to measure a full six degrees of freedom (DoF): three positional DoF and three angular DoF. In other embodiments, a single coil 305 may be disposed on or within the distal end with its axis oriented along the instrument shaft. Due to the rotational symmetry of such a system, such an arrangement of a single coil 305 may be insensitive to roll about its axis, so only five degrees of freedom may be detected in such an implementation. The EM coils 305 may be configured to provide EM data from which a navigation and localization system (see, e.g., the system 90 and the EM data 93 of FIG. 15) can determine or estimate the position of the instrument 300. In some embodiments, the EM coils 305 can be replaced with or used in addition to other types of positions sensors for detecting or determining the position of the instrument 300.

Figure 21:
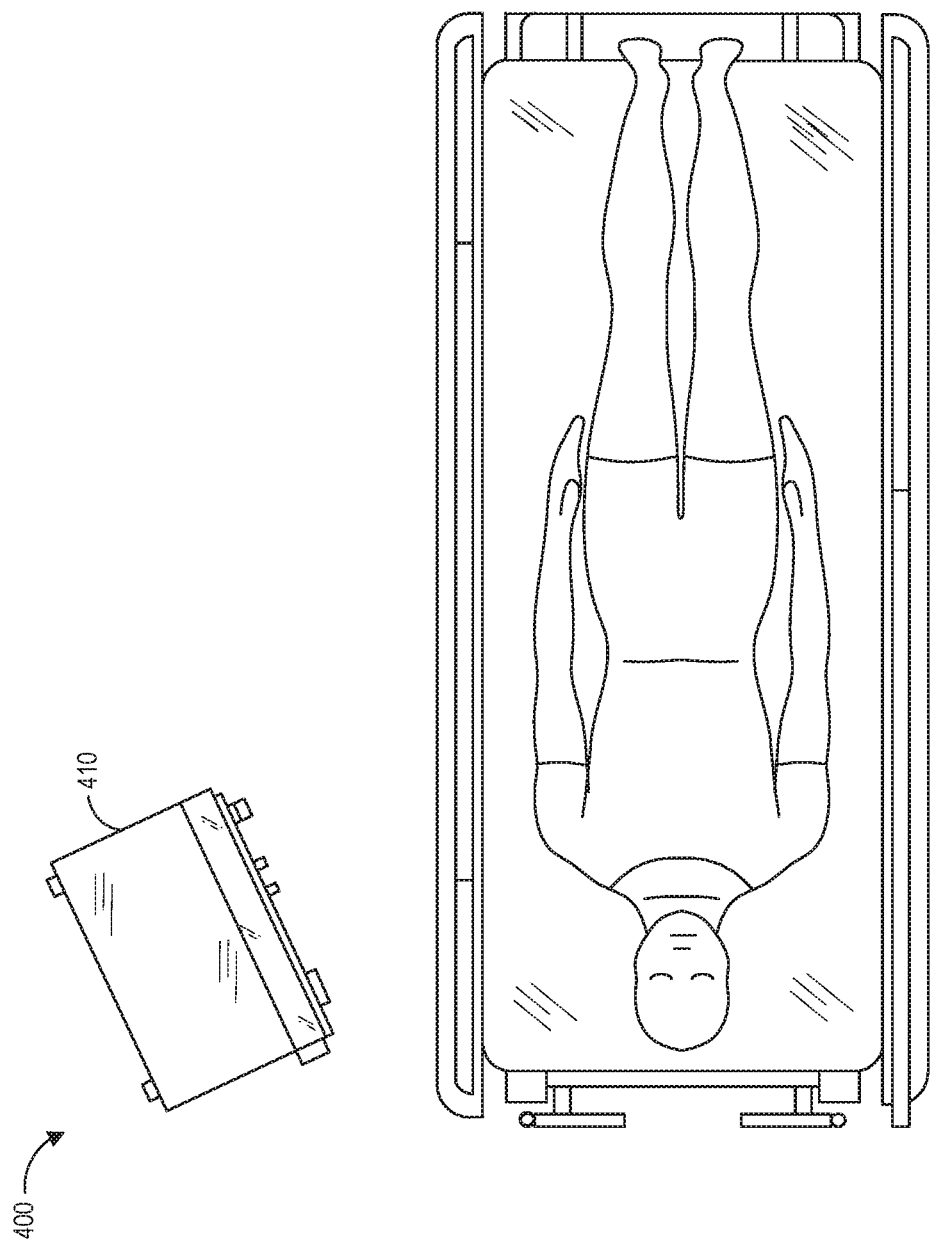
FIG. 21 illustrates certain components of an example electromagnetic (EM) system for determining position of a medical instrument.

FIG. 21 illustrates certain components of an example EM system 400 for determining position of a medical instrument based on EM data generated by EM coils 305. The system 400 can include an EM field generator 410 and EM coils 305 positioned on the instrument 300 (not shown). The system 400 can be implemented in an operating environment that includes a table for supporting a patient. Certain additional devices/elements may also be included, but have not been illustrated in FIG. 21. For example, the environment may also include: a robotic system configured to guide movement of the medical instrument, a command center/console for controlling operations of the surgical (or medical) robotic system, and an EM controller. The EM controller may further be connected to the EM field generator 410 to provide control signals thereto for generating an EM field. In certain embodiments, the EM controller may be partially or completely incorporated into one or more of the other processing devices of the system, including the EM field generator 410 and/or other devices in the environment (e.g., the cart 11 and/or the tower 30 illustrated in FIG. 1).

When included, the EM controller may control EM field generator 410 to produce an EM field. The EM field may be a varying EM field. For example, the EM field may be time-varying and/or spatially varying, depending upon the embodiment. The EM field generator 410 may be located on a cart, similar to the cart 11 illustrated in FIG. 2, or may be attached to a rail of the table via one or more supporting columns. In other embodiments, an EM field generator 410 may be mounted on a robotic arm, for example similar to those shown in surgical (or medical) robotic system 10 of FIG. 1, which can offer flexible setup options around the patient.

An EM spatial measurement system may determine the location of objects within the EM field that are embedded or provided with EM sensor coils, for example, the EM coils 305 (as shown in FIG. 20). When an EM sensor is placed inside a controlled, varying EM field as described herein, voltages are induced in sensor coil(s) included in the EM sensor. These induced voltages can be used by the EM spatial measurement system to calculate the position and orientation of the EM sensor and thus the object having the EM sensor. As the EM fields are of a low field strength and can safely pass through human tissue, location measurement of an object is possible without the line-of-sight constraints of an optical spatial measurement system.

The EM field may be defined relative to a coordinate frame of the EM field generator 410, and a coordinate frame of the model 150 of the luminal network 130 can be mapped (or registered) to the coordinate frame of the EM field. Thus, the position of the instrument, as determined by the position of the EM instrument sensors 305 on the instrument within the EM field can be determined within the coordinate frame of the model, but without relying on the model to determine the position.

The system 400 may thus return EM data 93 that can be used by the localization system 90 to determine the position of the instrument. As noted above, the EM data 93 can provide a modality that can be used to determine position in a coordinate frame that has been mapped or registered to the model 150.

Returning to FIG. 20, the instrument 300 may include the illumination sources 310, which provide light to illuminate a portion of an anatomical space. The illumination sources 310 can each be one or more light-emitting devices configured to emit light at a selected wavelength or range of wavelengths. The wavelengths can be any suitable wavelength, for example, visible spectrum light, infrared light, x-ray (e.g., for fluoroscopy), to name a few examples. In some embodiments, the illumination sources 310 can include light-emitting diodes (LEDs) located at the distal end of the instrument 300. In some embodiments, the illumination sources 310 can include one or more fiber optic fibers extending through a length of the instrument 300 to transmit light through the distal end from a remote light source, for example, an x-ray generator. For example, the distal end may include multiple illumination sources 310 configured to emit the same or different wavelengths of light as one another.

The imaging device 315 can include any photosensitive substrate or structure configured to convert energy representing received light into electric signals, for example, a charge-coupled device (CCD) or complementary metal-oxide semiconductor (CMOS) image sensor. Some examples of imaging device 315 can include one or more optical fibers, for example, a fiber optic bundle, configured to transmit light representing an image from the distal end of the instrument 300 to an eyepiece and/or image sensor located proximally relative to the distal end of the instrument 300. The imaging device 315 can additionally include one or more lenses and/or wavelength pass or cutoff filters for various optical designs. The light emitted from the illumination sources 310 allows the imaging device 315 to capture images, e.g., of the interior of a patient's luminal network. These images can then be transmitted as individual frames or a series of successive frames (e.g., a video) to a computer system or component(s) thereof, such as, e.g., a command console 500 shown in FIG. 22.

Figure 22:
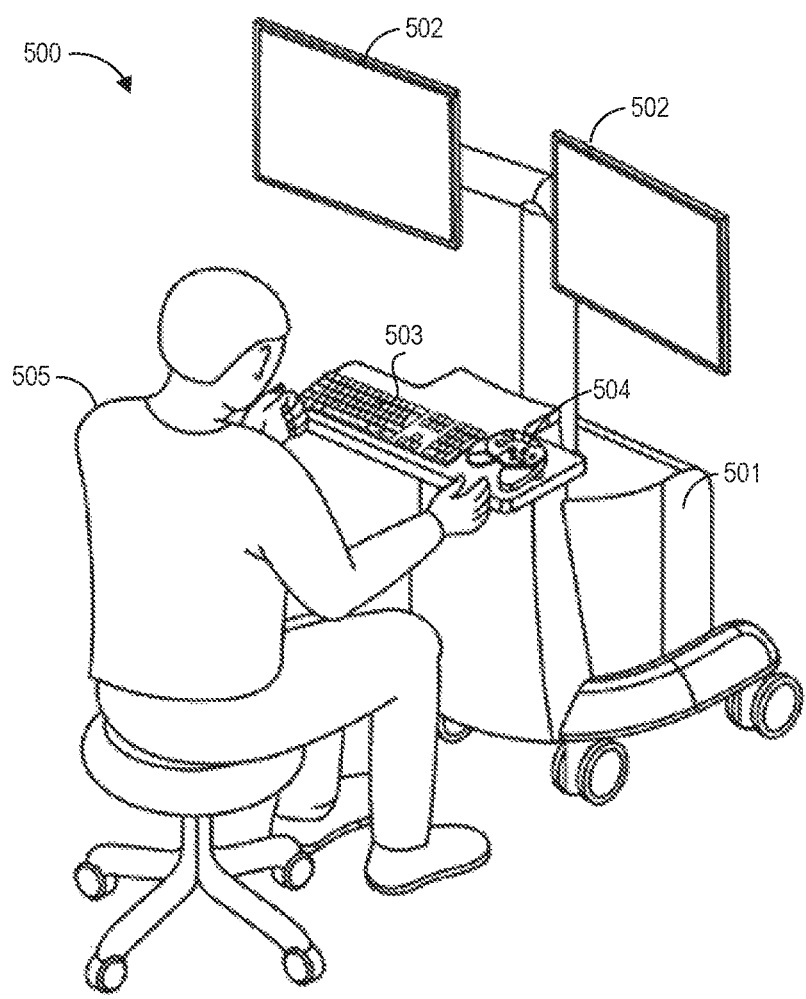
FIG. 22 illustrates an example command console, including a display, for an example medical robotic system, according to one embodiment.

FIG. 22 illustrates an example command console 500 that can be used with certain implementations of the systems described herein. As illustrated, in some embodiments, the command console 500 includes a console base 501, display(s) 502 (e.g., one or more monitors), and one or more control modules (e.g., a keyboard 503 and/or a joystick 504). A user 505 (e.g., a physician) can remotely control the robotic system and/or associated systems/sub-systems (e.g., the systems described with reference to FIGS. 1-15) using the command console 500 (e.g., from an ergonomic position). For example, the user 505 can use the command console 500 to navigate an instrument within a luminal network of the a patient. The command console 500 may also display information to the user 505 that can be used to aid in navigation of the luminal network.

The displays 502 may include electronic monitors (e.g., LCD displays, LED displays, touch-sensitive displays), viewing devices (e.g., goggles or glasses), and/or other display devices (e.g., virtual reality of viewing devices). In some embodiments, one or more of the displays 502 can display the model 150 of the patient's luminal network 130. The displays 502 can also display image information received from a camera or another sensing device positioned on the instrument within the luminal network 130. In some embodiments, a model or representation of the instrument is displayed with the model 150 to help indicate a status of a surgical or medical procedure.

In some embodiments, the console base 501 includes a central processing unit (CPU or processor), a memory unit (computer-readable memory), a data bus, and associated data communication ports that are responsible for interpreting and processing signals such as camera imagery and tracking sensor data, e.g., from a medical instrument positioned within a luminal network of a patient. In some instances, the techniques for instrument navigation and targeting described herein are executed by the processor of the console base 501. The console base 501 may also process commands and instructions provided by the user 505 through the control modules 503, 504. In one example, as noted above and shown in FIG. 22, the control module 503 may comprise a keyboard and the control module 504 may comprise a controller. The control modules may include other devices, such as computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, irrigation, etc.). Using the control modules 503, 504 of the console base 500, the user 505 may navigate an instrument through the luminal network 130. One or more of control modules 503 and 504 may be configured to provide haptic feedback to the user via, for example, a haptic engine.

C. Example Skeleton-Based Luminal Network Modelling and Navigation.

Figure 23:
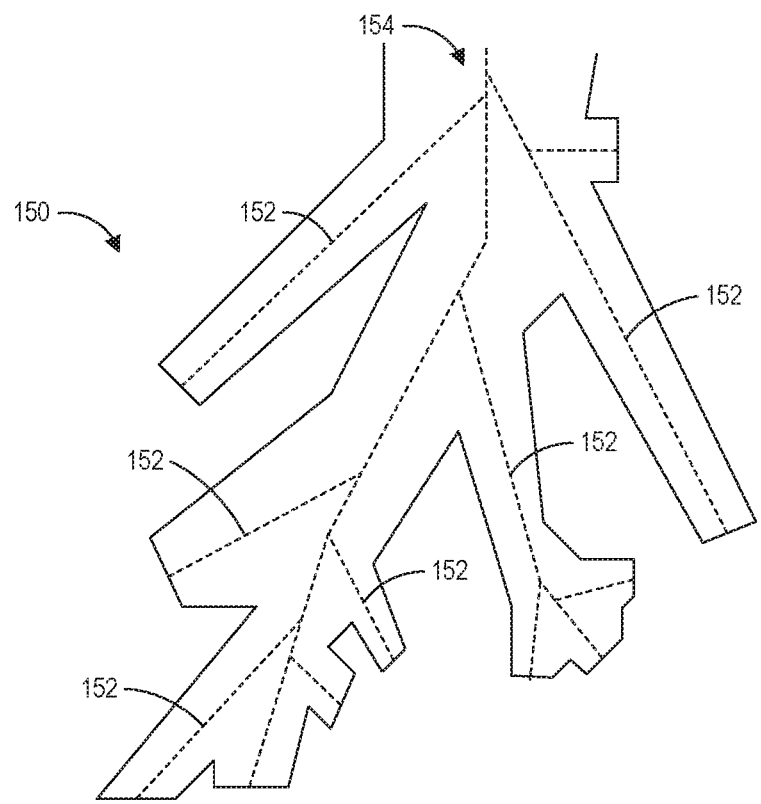
FIG. 23 illustrates an example skeleton-based model of a portion of a luminal network.

FIG. 23 illustrates an example skeleton-based model of a portion of a luminal network. In particular, the skeleton-based model 150 illustrates an implementation in which the luminal network 130 is modelled as a "skeleton" 154 which may comprise a plurality of discrete segments 152. The model 150 illustrated in FIG. 23 may be used by a localization system 90 (see FIG. 15) to calculate the position and orientation of the distal end of a medical instrument. Each segment 152 of the model may be assigned a unique "segment ID" and each of the segments 152 forming the skeleton 154 may be defined with respect to a center line of the corresponding lumen (e.g., lumen 132 in FIG. 16) in the model 150 of the luminal network 130. During certain medical procedures, the medical instrument may be navigated through the luminal network 130 for at least a portion of the medical procedure. Thus, while the distal end of the medical instrument is within a volume defined by the model 150, the position of the distal end of the medical instrument may be estimated by the localization system 90 as a point along the skeleton 154.

The system may define the position of the distal end of the medical instrument using the model 150 including the skeleton 154. For example, the position may be defined by identifying a segment 152 corresponding to the lumen 132 (of the luminal network 130) in which the distal end of the medical instrument is positioned and determining the depth of the distal end of the medical instrument along the segment 152. Accordingly, the position of the distal end of the medical instrument may be defined by two pieces of information—namely, the segment ID of the segment 152 and the depth of the distal end along the segment 152. The system may calculate the position of the distal end of the medical instrument as being along the identified segment 152. While the diameter of a lumen may be larger than that of the medical instrument near the access point, as the medical instrument is advanced further into the luminal network 130, the diameters of the lumens of the airway branches corresponding to each of the segments 152 may be similar in size to the diameter of the medical instrument. Thus, selecting a point along the skeleton 154 as the position for the distal end of the medical instrument may have sufficient accuracy for navigational purposes. The orientation of the distal end of the medical instrument may be determined using position/orientation data, such as, for example, EM data measured using EM position sensors 305 data generated by a shape sensing fiber located within the medical instrument, etc.

Figure 24A:
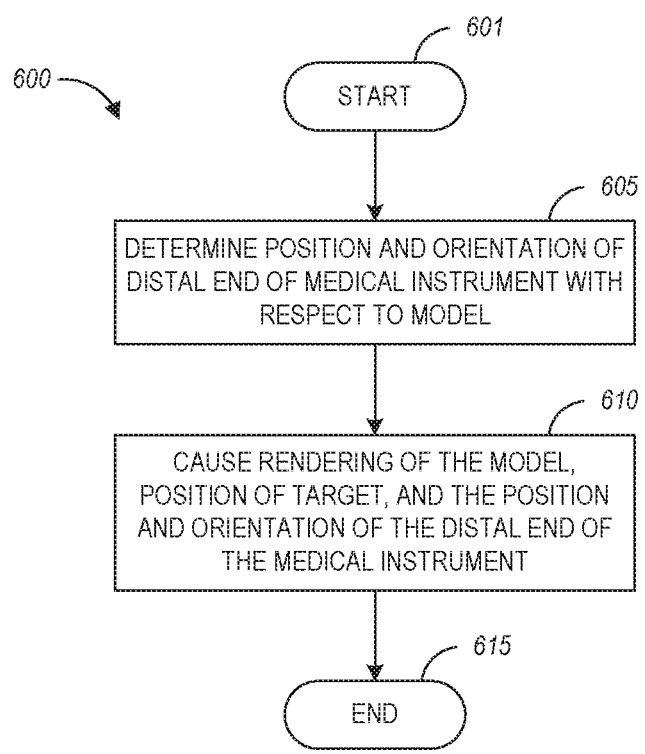
FIG. 24A is a flowchart illustrating an example method of rendering one or more views for medical instrument navigation in accordance with aspects of this disclosure.

FIG. 24A is a flowchart illustrating an example method operable by a surgical robotic system, or component(s) thereof, for rendering one or more views for medical instrument navigation in accordance with aspects of this disclosure. For example, the steps of method 600 illustrated in FIG. 24A may be performed by a processor of a surgical robotic system. For convenience, the method 600 is described as performed by the processor of the system.

The method 600 begins at block 601. The processor may be included as a part of a system, including a medical instrument (e.g., the instrument 300 of FIG. 20) having an elongate body and at least one sensor (e.g., the EM sensor 305 of FIG. 20), a display, a processor, and a memory storing a model (e.g., model 150 of FIG. 17, 18 or 23) of a mapped portion of a luminal network and a position of a target with respect to the model. At block 605, the processor determines, based on data from the at least one sensor, a position and orientation of a distal end of the medical instrument with respect to the model. At block 610, the processor causes, on at least a portion of the display, a rendering of the model, the position of the target, and the position and orientation of the distal end of the medical instrument. The rendering may be based on a viewpoint directed at the target and different from a viewpoint of the medical instrument. The method 600 ends at block 615.

Figure 24B:
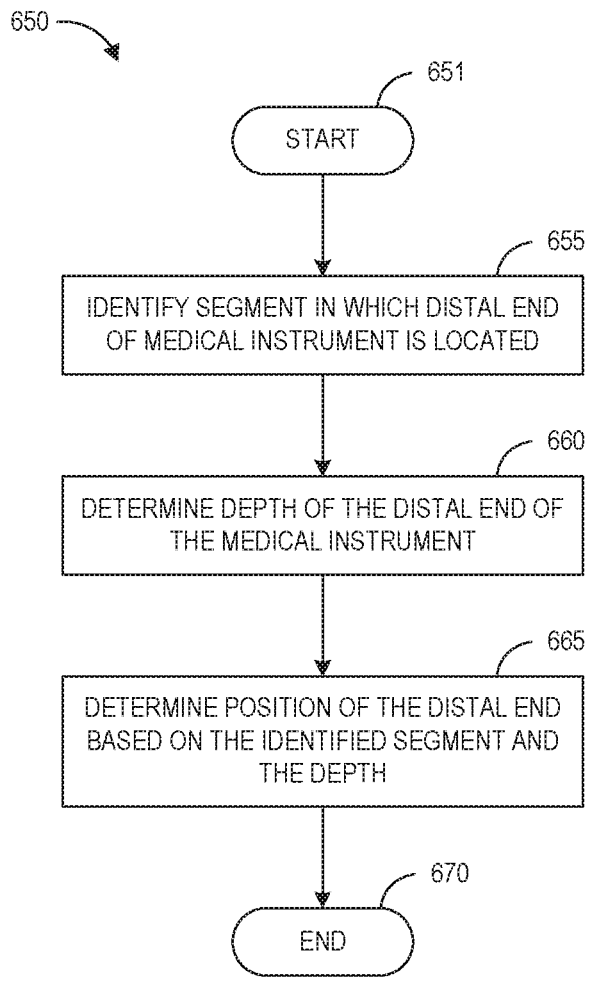
FIG. 24B is a flowchart illustrating another example method for determining position of a medical instrument within a luminal network using a skeleton-based model in accordance with aspects of this disclosure.

FIG. 24B is a flowchart illustrating another example method for determining a position of a medical instrument within a luminal network using a skeleton-based model in accordance with aspects of this disclosure. The method 650 may be implemented in certain robotic systems, such as the robotic systems illustrated in FIGS. 1-15 and others. The method 650 may be implemented in or by a navigation system, such as the navigation or localization system 90 of FIG. 15. In some embodiments, one or more computer devices may be configured to execute the method 650. The computer devices may be embodied by a processor (or processors) and computer-readable memory in one or more components discussed above. The computer-readable memory may store instructions that may be executed by the processor(s) to perform the method 650. The instructions may include one or more software modules. By way of example and not limitation, the computer devices may be in the tower 30 shown in FIG. 1, the cart shown in FIGS. 1-4, the beds shown in FIGS. 5-10, the command console 500 shown in FIG. 22, one or more of the displays 502 shown in FIG. 22, etc.

The method 650 begins at block 651. The method 650 may be executed, for example, as a medical instrument is navigated through a luminal network 130, for example, as shown in FIG. 18. The method 650 may thus be triggered, in some embodiments, when the medical instrument is introduced into the luminal network 130. In some embodiments, the method 650 may be triggered manually, for example, when a user input or command is received. In some embodiments, the method 650 is executed when the distal end of the medical instrument is located with a mapped portion (e.g., within a model such as model 150) of a luminal network 130. As mentioned above, the method 650 can be implemented for navigation of a wide variety of luminal networks, included branched luminal networks (such as bronchial networks, renal networks, cardiovascular networks (e.g., arteries and veins), etc.) and non-branched (e.g., single lumen) luminal networks (such as gastrointestinal tracts, urinary tracts, etc.).

The method 650 may involve determining the position of a distal end of a medical instrument within a model 150 of a luminal network 130. The model 150 may include a skeleton (e.g., the skeleton 154) including a plurality of segments (e.g., the segments 152). Each of the segments may be defined with respect to a center line of a corresponding lumen of the mapped portion of the luminal network. The model 150 including the skeleton 154 may be constructed based on preoperative (and/or intraoperative) images (e.g., CT scans) of the luminal network 130. At block 655, the system identifies a segment in which the distal end of the medical instrument is located. The system may determine a state (e.g., a segment ID and depth along the segment) of the distal end of the medical instrument using one or more types of input data (e.g., model data 91, vision data 92, EM data 93, and/or robotic command and kinematics data 94). The position and/or orientation of the distal end of the medical instrument may be determined based on the state.

At block 660, the system may determine the depth of the distal end of the medical instrument along the skeleton of the segment identified in block 655. In one implementation, the system may calculate the length of the medical instrument inserted into the patient based on the robotic command and the kinematics data 94 and determine the depth of the distal end of the medical instrument along the calculated path from the access point to the identified segment. The system may then determine the depth of the distal end of the medical instrument along the identified segment based on the path and depth data. In other embodiments, the depth of the distal end of the medical instrument may be identified based on the model data 91, the vision data 92, the EM data 93, and/or the robotic command and kinematics data 94 without the use of the path data. At block 665, the system may determine the position of the distal end of the medical instrument based on the identified segment and the determined depth. The position of the distal end of the medical instrument may be determined to lie along the skeleton of the identified segment at the determined depth. In certain implementations, in response to determining that the position of the distal end of the medical instrument is within a volume defined by the model, the system may restrict the determined position of the distal end of the medical instrument to be located along the skeleton. The method 650 ends at block 670.

The position determined based on the skeleton-based model 150 may be used in a number of different navigation-related targeting applications. For example, the system may determine a distance between the distal end of the medical instrument and a target based on the determined position of the distal end of the medical instrument and the position of the target. The position of the target may be determined based on preoperative CT scans or selected by a user of the surgical robotic system based on intraoperative CT scans of the luminal network. For example, the system may determine the Euclidean distance between the position of the distal end of the medical instrument and the position of the target.

As discussed in greater detail below, the system may render the position of the distal end of the medical instrument with respect to the model on a display. The rendered position of the distal end of the medical instrument may be based on the position determined using the skeleton-based model of the luminal network, as discussed above.

Certain aspects of this disclosure relating to the use of skeleton-based navigation may improve the system's accuracy in locating the distal end of the medical instrument, when the distal end of the medical instrument is located within a model of a luminal network. For example, as discussed in connection with FIG. 15, a localization system 90 may use a plurality of types of input data (e.g., model data 91, vision data 92, EM data 93, and/or robotic command and kinematics data 94) to determine the position of the distal end of the medical instrument. By estimating the position of the distal end of the medical instrument to be located on the skeleton (e.g., by defining the position with respect to an identified segment in the model and a depth along the center line of the identified segment), errors in the estimation of the position of the distal end of the medical instrument without the use of the skeleton based model may be reduced. As discussed above, this may result from the high likelihood that the distal end of the medical instrument is located within the luminal network when the distal end of the medical instrument is within the mapped portion of the luminal network.

One potential source of error that may be corrected by using the skeleton-based model is error due to tissue deformation. For example, when a lumen is deformed from its mapped position (which may be determined preoperatively), the position of a portion of the lumen may be displaced from the mapped position of the portion of the lumen. Such a deformation may occur due to forces on the lumen from the medical instrument and/or natural biological processes, etc. During a deformation, the input data may indicate that the position of the distal end of the medical instrument has moved outside of the luminal network. By estimating the position of the distal end of the medical instrument to be located along the skeleton of the model, such deformation errors may be reduced.

The use of a plurality of types of input data in localizing the distal end of the medical instrument, in addition to the skeleton-based model, may provide an improvement over localization methods that use a single type of input data. However, aspects of this disclosure may also be applied to localization systems using a single type of input data. Single input data systems (e.g., an EM only system, a vision-only system, or a shape sensing fiber), may be more susceptible to certain errors, such as the types of distortion errors discussed above. By combining such single input data systems with a skeleton-based model, these errors may be reduced. The system may be configured, in certain embodiments, to determine the position data representative of the distal end of the medical instrument, based only on data received from a single sensor (e.g., from one of an EM sensor or a shape sensing fiber).

D. Example Rendered Views for Medical Instrument Navigation.

Figure 25:
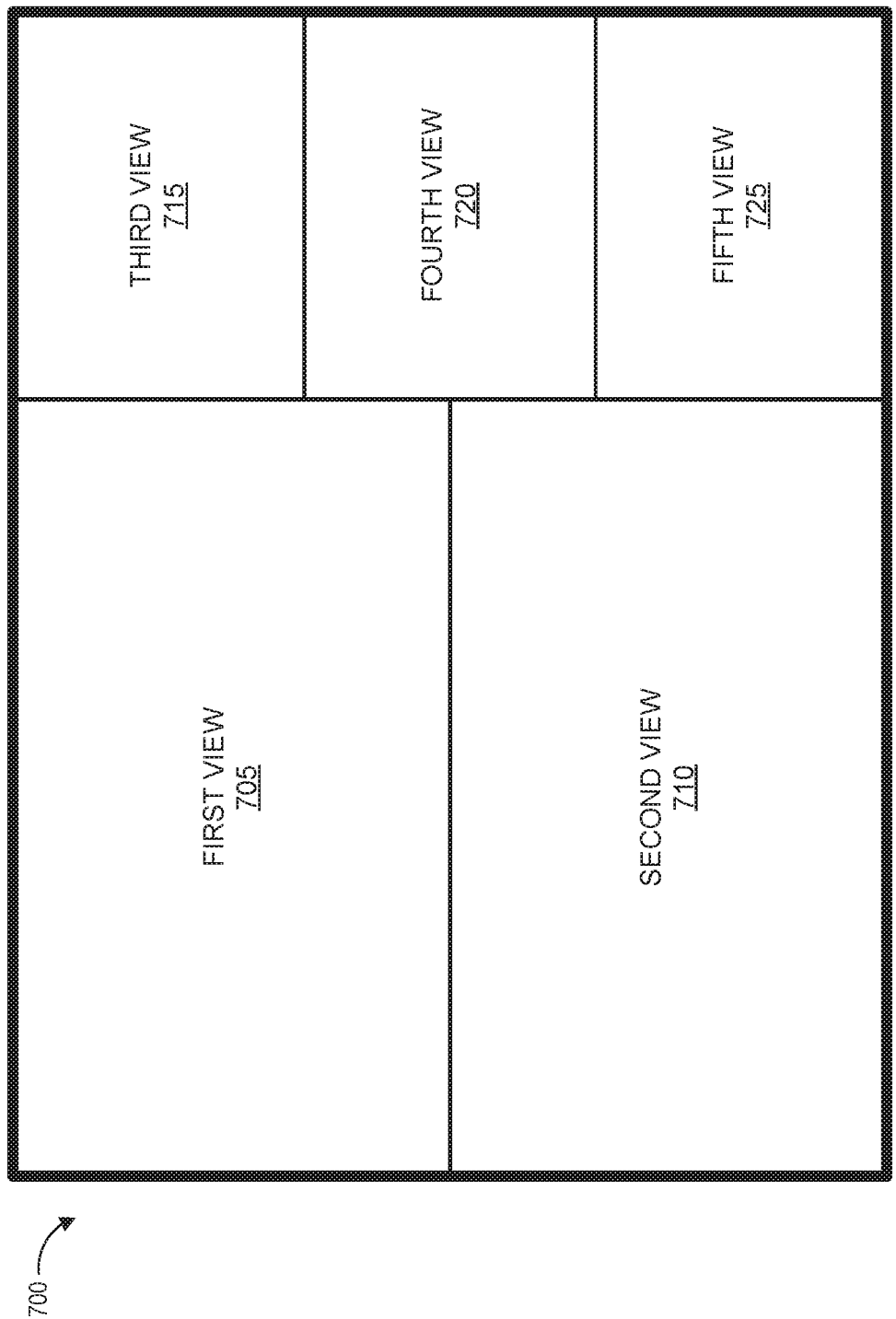
FIG. 25 illustrates an example of a rendered image displayed to provide navigational feedback to a user of a robotic system in accordance with aspects of this disclosure.

FIG. 25 illustrates an example of a rendered image displayed to provide navigational feedback to a user of a robotic system in accordance with aspects of this disclosure. The image 700 illustrated in FIG. 25 may be rendered on a display such as display 502 illustrated in FIG. 22. In other embodiments, the image 700 may also rendered using one or more other display technologies, such as a projector (e.g., a holographic image projector), a wearable display (e.g., a head-mounted display such as augmented reality glasses or a virtual reality headset), 3D monitors (e.g., high-frequency monitors), etc. Certain robotic surgical systems may provide one or more rendered images to provide location and/or guidance information to a user of the system to aid in the navigation of a medical instrument during a medical procedure. In the example of FIG. 25, the rendered image includes first through fifth views 705-725, each of which may render visual information providing location and/or navigational guidance information. Although five views 705-725 have been illustrated in the rendered image 700, any number of views may be rendered, and the location, size, number of views, etc., may be selected or modified by the user in certain implementations.

One or more of the first to fifth views 705-725 may be generated based on preoperative and/or intraoperative data. For example, two of the views 705-725 may provide scans of a luminal network and may represent the position of at least a portion of a medical instrument within the luminal network. Other views may provide a rendered view of images captured with an imaging device positioned on the medical instrument, such as imaging device 415 of FIG. 20. The scans and/or imaging device captured images may provide the user with a substantially real-time representation of the position of the distal end of the medical instrument.

Aspects of this disclosure relate to the rendering of additional images which may be virtually rendered based on a model of the luminal network, the medical instrument, and/or a target. As discussed above, the system may generate a model (e.g., model 150 of FIG. 17, 18 or 23) of the luminal network based on preoperative and/or intraoperative scans of the luminal network. Further, the system can determine the position of a distal end of the medical instrument based on one or more types of input data (e.g., model data 91, vision data 92, EM data 93, and/or robotic command and kinematics data 94). Thus, a visual representation of the model, a position and/or orientation of the distal end of the medical instrument, and a target may be rendered for display in at least a portion of a display (e.g., in one of the first to fifth views 705-725 in the rendered image 700).

Additionally, textual and/or visual information may be overlaid on a portion of the display to aid in navigation. For example, based on the determined position and orientation of the distal end of the medical instrument and the position of the target, the system may determine and display one or more of: a distance between the distal end of the medical instrument and the target, and an angle between an insertion direction of the medical instrument and the target. Embodiments of the types of additional information that may be provided will be discussed in detail below.

Figure 26:
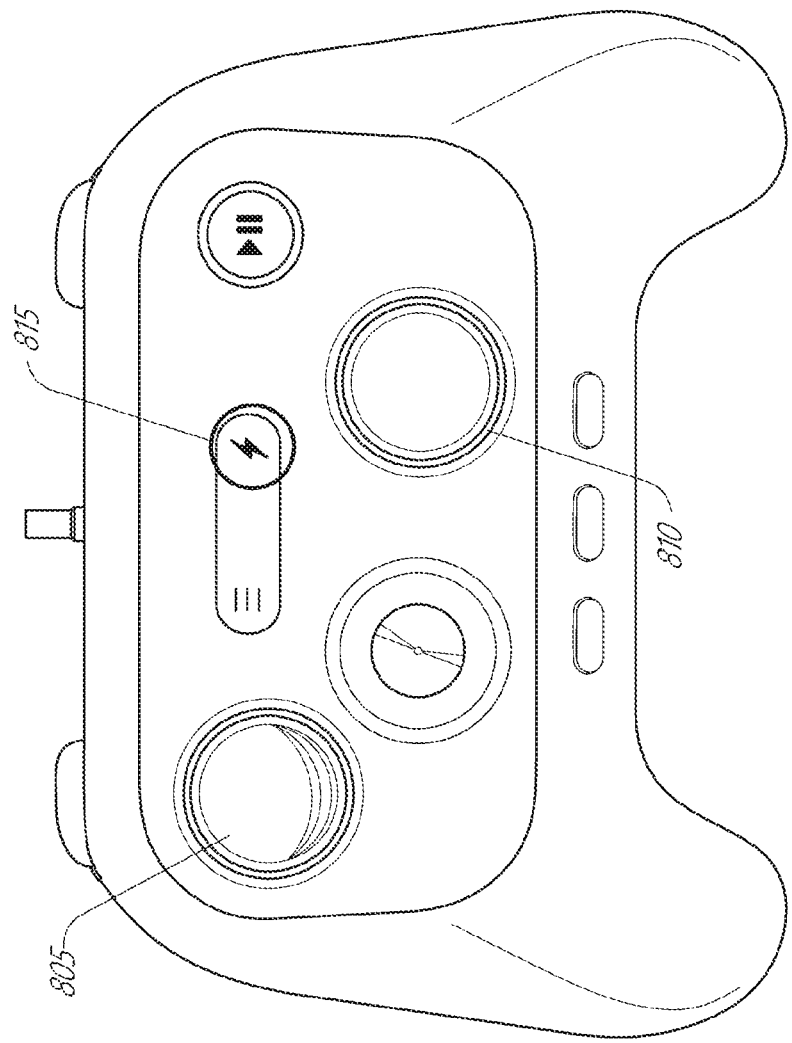
FIG. 26 illustrates an example of an input device which may be used to receive input from a user in accordance with aspects of this disclosure.

A user of the system may provide instructions to control the movement of the medical instrument and/or adjust one or more aspects of the rendered image 700 using an input device 800. FIG. 26 illustrates an example of an input device which may be used to receive input from a user in accordance with aspects of this disclosure. The input device 800 (e.g., a controller) may comprise a plurality of user input elements 805-815. User input elements 805 and 810 may be configured to receive user input instructions related to the movement of the distal end of the medical instrument, such as instructions to advance/retract and/or articulate the distal end of the medical instrument. The user input element 815 may be configured to receive user input instructions to modify one or more views rendered on a display.

In the example of FIG. 26, the user input element 815 may be a button configured to be actuated by a user. However, other embodiments may comprise other types of input elements, such as a joystick having one or more axes, trigger buttons, etc. In the context of a surgical robotic system, a more simplified control scheme may reduce the cognitive load of the user, enabling the user to focus on the more procedure-critical aspects of controlling the system during a medical procedure. For example, the user may be controlling the movement of the distal end of the medical instrument using the user input elements 805 and 810. Thus, by linking selection or modification of certain views rendered within the display to a single button, the user may be less likely to confuse control of the movement of the medical instrument with modification of the displayed views. As such, in certain embodiments, modification of one or more views rendered on the display may be mapped to certain types of user interaction with the user input element 815. Examples of possible types of user interaction include actuation of the user input element 815 for less than a first threshold period of time, actuation of the user input element 815 for greater than the first threshold period of time, actuation of the user input element 815 twice within a second threshold period of time, etc. Other implementations may include a plurality of user input elements, each user input element mapped to one or more instructions for modifying the rendered view.

Figure 27:
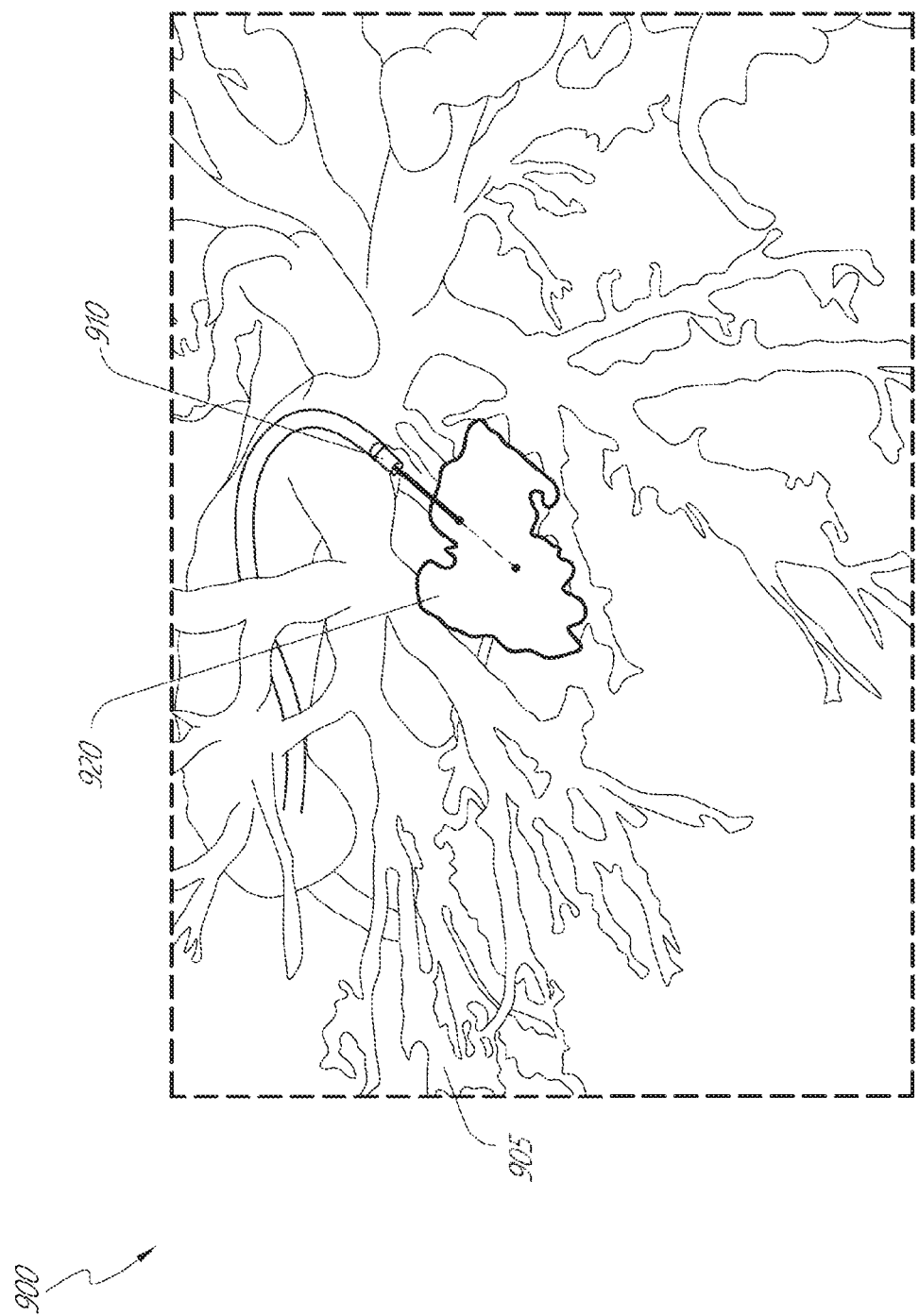
FIG. 27 is an example of a rendered view of a medical instrument within a model of luminal network in accordance with aspects of this disclosure.
Figure 28A:
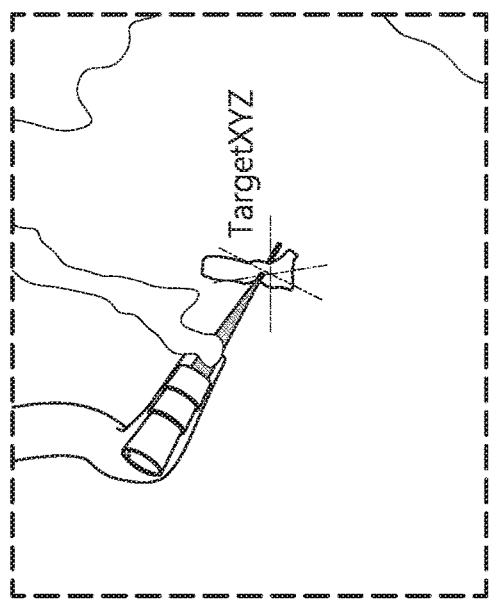
FIGS. 28A-28D illustrate a series of modified rendered views generated based on a rotation instruction in accordance with aspects of this disclosure.
Figure 28B:
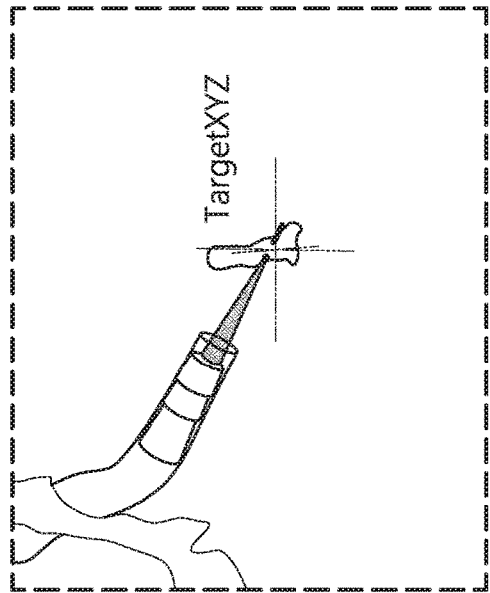
Figure 28C:
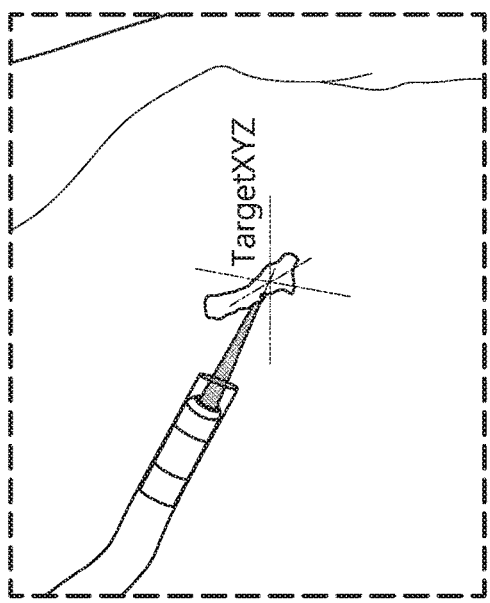
Figure 28D:
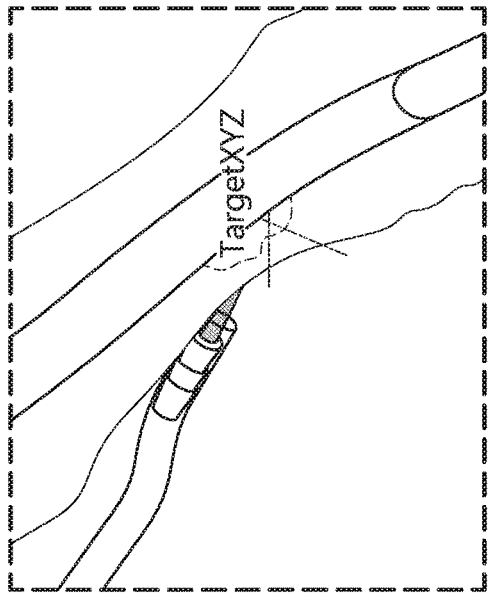

FIG. 27 is an example of a rendered view which may be displayed during a medical procedure in accordance with aspects of this disclosure. In particular, the view 900 may be rendered within at least a portion of a display to provide a visualization of the relative position of a distal end 910 of a medical instrument within a model 905 of a luminal network. The rendered view 900 may also include a target 920 (e.g., a target nodule for a biopsy procedure). The target 920 may be a region within or adjacent to the model 905 and the medical procedure may involve driving the distal end 910 of the medical instrument within a threshold distance of the target 920. In the biopsy example, one or more tools (e.g., a biopsy needle) may be deployed from the medical instrument to retrieve one or more tissue samples from the target 920 when within the threshold distance from the target 920. In this example, the target 920 may be a lesion or nodule within the lungs of a patient.

As discussed above, the model 905 and target 920 may be generated based on preoperative and/or intraoperative scans of the luminal network (e.g., CT scans, MRI, etc.). For certain medical procedures, the medical instrument may have an elongate body configured to navigate the luminal network until within a threshold distance of the target 920. The medical instrument may comprise at least one sensor (e.g., EM sensor coils 305 and/or imaging device 415, see FIG. 20) which may be positioned at or near the distal end 910 of the medical instrument and configured to produce an output signal. The system may be configured to generate data indicative of the position of the distal end 910 of the medical instrument based on the signal output from the at least one sensor. The system may be configured to determine, based on the position data, the position and/or orientation of the distal end 910 of the medical instrument with respect to the model 905. In certain embodiments, the system may determine the position and/or orientation of the distal end 910 of the medical instrument based on a skeleton-based model of the luminal network, as discussed above. Accordingly, the system may determine the position of the distal end 910 of the medical instrument based on an identified segment of the model and a determined depth of the distal end 910 of the medical instrument along the skeleton of the identified segment.

The system may then cause, on at least a portion of a display, a rendering of the model 905, the position of the target 920, and the position and orientation of the distal end 910 of the medical instrument. One example of such a rendering is illustrated in FIG. 27. In certain implementations, the rendering is based on a viewpoint directed at the target 920 and different from a viewpoint of the medical instrument. As used herein, the term "viewpoint" generally refers to the location with respect to the rendered image from which the rendered image is viewed.

In one example, the rendered image may be centered on the target 920 rather than centered on the distal end 910 of the medical instrument. As discussed above, the rendering may be displayed on a portion of a display in addition to other views, such as the images captured by an imaging device located on the distal end 910 of the medical instrument. To provide a complementary visualization of the medical procedure to the images captured by the imaging device, the rendered view 900 may be generated from a "third-person" perspective viewpoint with respect to the distal end 910 of the medical instrument. In this example, images captured by the imaging device may be considered a "first-person" viewpoint from the perspective of the distal end 910 of the medical instrument.

Due to the shape of the model 905, the viewpoint from which the rendered view 900 is generated may affect the objects that are visible in the rendered view 900. For example, portions of the model 905 closer to the viewpoint may obstruct the view of other object located behind the closer portions. When portions of the model 905 along which the user intends to drive the medical instrument or the target are obstructed from view, the rendered view 900 may not assist the user in navigating the medical instrument. Accordingly, the system may be configured to modify the viewpoint of the rendered image 900 based on the actuation of a user input element (e.g., user input element 815 of FIG. 26) to bring obstructed objects into view. In another embodiment, the system may be configured to render at least a portion of the model 905 semi-transparent (or alternatively fully-transparent) when the portion of the model 905 obstructs the view of one or more other rendered objects.

In one implementation, the system may be configured to receive, via a user input element, a first type of user interaction with the user input element. The system may then generate a first type of rendering instruction based on the first type of user interaction with the user input element. In response to generating the first type of rendering instruction, the system may cause within the portion of the display a modified view of the model, the position of the target, and the position and orientation of the distal end of the medical instrument.

In certain embodiments, the system may employ algorithms such as fuzzy logic or machine learning to automatically select a method for modifying the view of the model. For example, the system may use the user's inputs during a medical procedure to determine the user's preferences for a particular viewpoint during the medical procedure. In some embodiments, the system may adaptively adjust the viewpoint on a user-by-user basis, and thus, use only previous input for the current user to determine how to adjust or modify the rendered image. In other embodiments, the system may infer user behavior for a plurality of users, pooling the user input data to generate global statistics that may be used to automatically generate a modified view. The global statistics and user-specific statistics may also be weighted to create a user-specific algorithm which additionally incorporates certain statistics from the pool of users.

As described above, the system may be able to detect a plurality of different user interaction types when the user interacts with the user input element. The system may map each of the types of user interaction with the user input element to different modifications of the rendered view 900. For example, the system may generate different types of rendering instructions corresponding to each of the types of detectable user interaction with the user input element. Thus, the system may generate a first type of rendering instruction in response to a first type of user interaction with the user input element.

In one implementation, the first type of rendering instruction may include a rotation instruction to rotate the viewpoint directed at the target. The modified view may include a rotated view of the model, the position of the target, and the position and orientation of the distal end of the medical instrument, with the target as a center of the rotation. Thus, the viewpoint of the rendered view 900 may rotate around the target in response to the rotation instruction.

FIGS. 28A-28D illustrate a series of modified rendered views generated based on a rotation instruction in accordance with aspects of this disclosure. In one embodiment, the first type of user interaction may include the user actuating the user input element for longer than a threshold period of time. For example, the user may press (e.g., hold down) a button for longer than the threshold period of time. Once the button has been actuated for a length of time greater than the threshold period of time, the system may initiate a rotation of the viewpoint of the rendered view. The system may continue rotating the rendered view while the button remains actuated. Once the button is released, the system may halt the rotation of the viewpoint of the rendered view.

As shown in FIGS. 28A-28D, each of the rendered views generated in response to the rotation instruction may be generated having a viewpoint that forms a predetermined angle with a rotation axis passing through the target around which the view is configured to rotate. For example, as shown in FIGS. 28A-28D, a coordinate system may be defined with the target at the origin. Each of the views in FIGS. 28A-28D may be rotated around the rotation axis passing through the center of the target. Additionally, the viewpoint at each of the rendered views may form the same angle with the axis around which the viewpoint rotates.

However, since the angle between the viewpoint and the reference plane is constant in the example of FIGS. 28A-28D, certain obstructed object may still be difficult to view in the rendered images using only the rotation instruction. Thus, the system may detect a second type of user interaction with the user input element. For example, the system may generate a second type of rendering instruction based on the second type of user interaction with the user input element. In some implementations, the second type of rendering instruction comprising an elevation instruction to alter the angle between the rotation axis and the viewpoint directed at the target. In response to generating the second type of rendering instruction, the system may cause within the portion of the display a rendering of the model having an altered angle between the rotation axis and the viewpoint directed at the target.

Figure 29A:
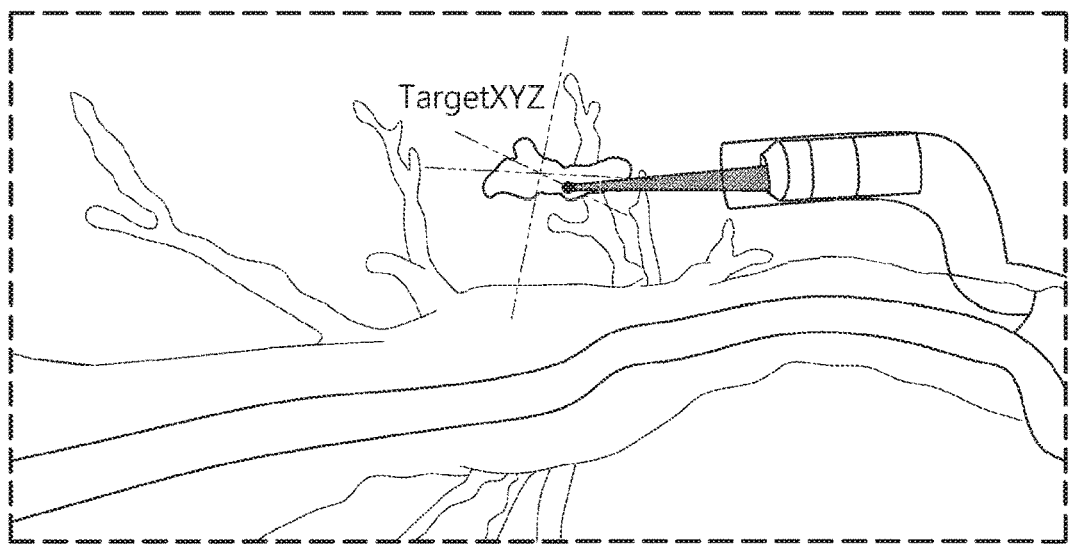
FIGS. 29A and 29B illustrate a series of modified rendered views generated based on an elevation instruction in accordance with aspects of this disclosure.
Figure 29B:
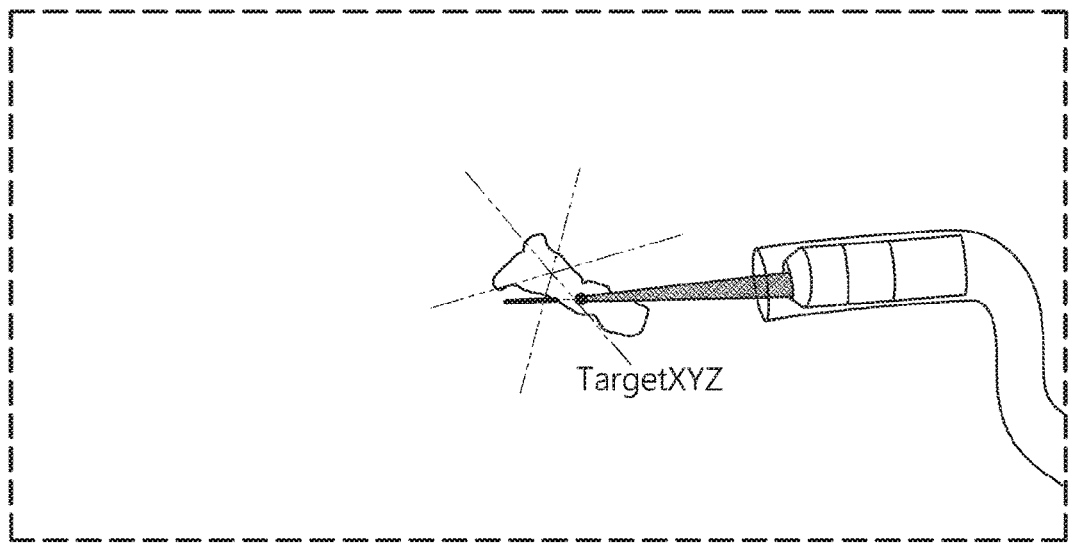

FIGS. 29A and 29B illustrate a series of modified rendered views generated based on an elevation instruction in accordance with aspects of this disclosure. In one embodiment, the second type of user interaction may include the user actuating the user input element for less than the threshold period of time. For example, the user may press and release the button before the threshold period of time has elapsed. Once the system detects the second type of user interaction, the system may initiate a change in the elevation of the viewpoint of the rendered view. The system may alternate between two or more predetermined elevation angles each time the system detects the second type of user interaction.

Figure 30:
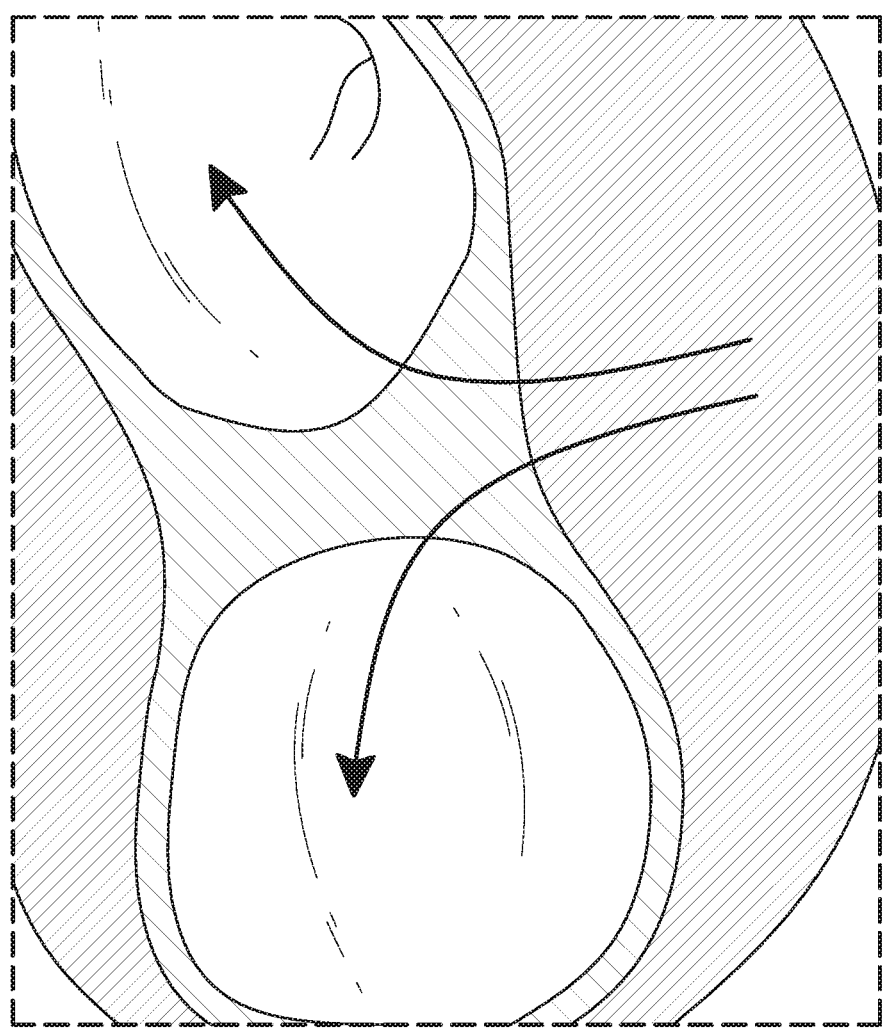
FIG. 30 illustrates a modified rendered view generated based on a toggle perspective instruction in accordance with aspects of this disclosure.

The system may also detect a third type of user interaction with the user input element. For example, the third type of user interaction may be a "double-click" tap(s), or similar gesture(s), where the button is actuated within a threshold period of time (which may be different than the threshold used for detecting the first and second types of user interaction). FIG. 30 illustrates a modified rendered view generated based on a toggle perspective instruction in accordance with aspects of this disclosure. For example, the system may toggle between the "third-person" rendered view (as illustrated in FIGS. 27-29) into a "first-person" rendered view from the viewpoint of the distal end of the medical instrument. The system may generate a third type of rendering instruction based on the third type of user interaction with the user input element. The third type of rendering instruction may include a toggle perspective instruction, configured to toggle the displayed viewpoint of the rendered model. The toggling of the viewpoint may include changing the viewpoint from the current viewpoint (e.g., a viewpoint that is different from the viewpoint of the medical instrument) to the viewpoint of the medical instrument. In response to generating the third type of rendering instruction, the system may cause within the portion of the display a rendering of the of the model from the viewpoint of the medical instrument. In other embodiments, the system may be configured to toggle between the "third-person" rendered view and the "first-person" rendered view in response to detecting the first type of user interaction (e.g., actuating the user input element for longer than a threshold period of time).

The rendered image based on the viewpoint of the medical instrument may provide the user with a visual representation of the interior of the luminal network, corresponding to images taken by an imaging device located on the distal end of the medical instrument. In certain circumstances, the images generated by the imaging device may be difficult for a user of the system to decipher due to the shape of the luminal network, the poor reflection of light emitted from illumination sources back to the imaging device, and/or material(s) (e.g., blood, dirt, pathology, etc.) blocking the view of the imaging device. Accordingly, the user may reference a rendering of the model from the viewpoint of the distal end of the medical instrument to the images captured by the imaging device to aid in navigation.

Figure 31:
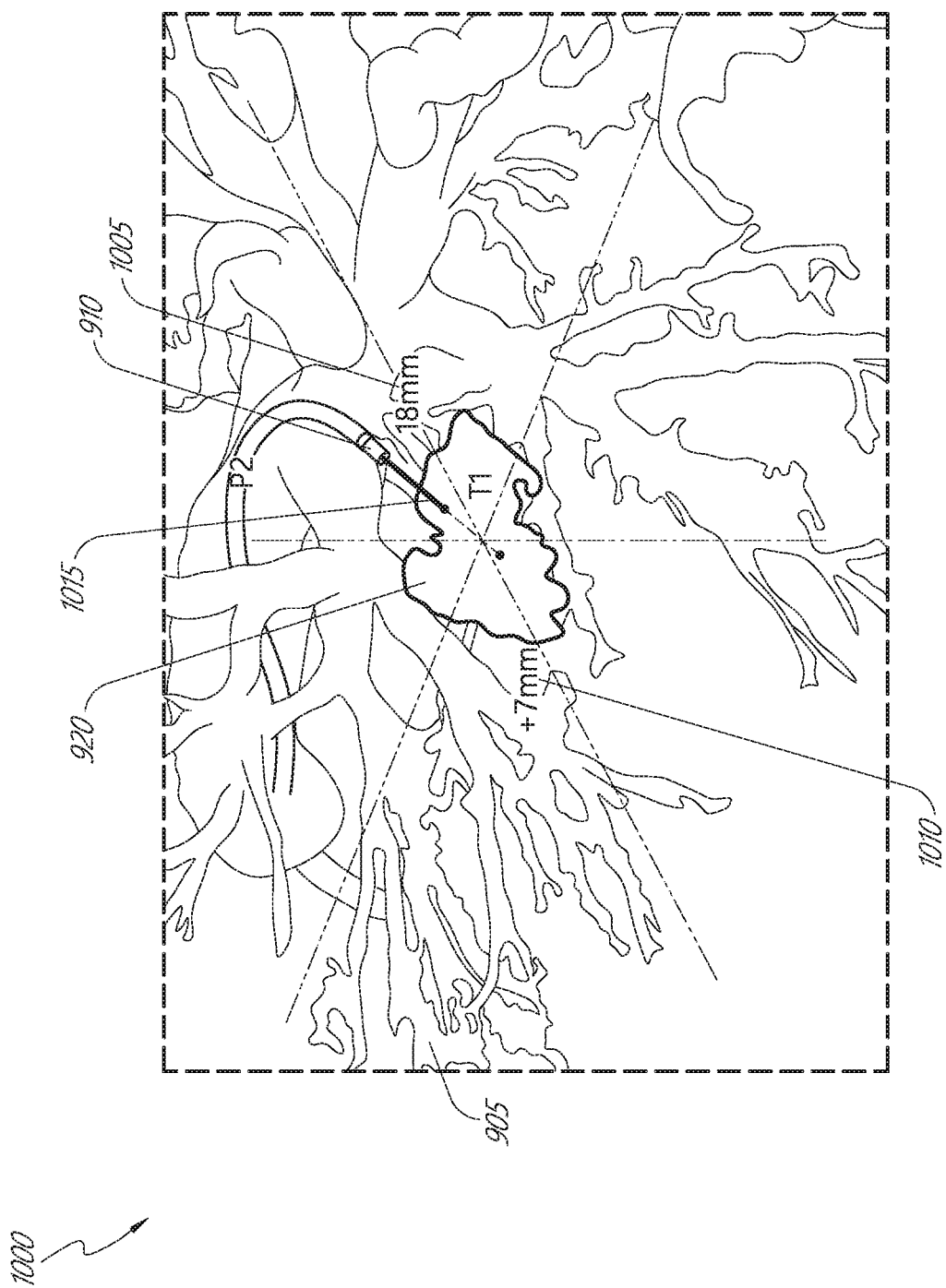
FIG. 31 is yet another example of a view which may be rendered on a display during a medical procedure in accordance with aspects of this disclosure.

The system may also provide additional visualization and/or text description, overlaid on one or more rendered images, to aid in the navigation of the medical instrument. FIG. 31 is yet another example of a rendered view which may be displayed during a medical procedure in accordance with aspects of this disclosure. The rendered image 1000 includes a first indication 1005 of the distance between the distal end 910 of the medical instrument and a surface (also referred to as a "boundary surface" or simply "boundary") of the target 920 along current insertion direction of the medical instrument. The rendered image 1000 also includes a second indication 1010 of the thickness of the target 920 along current insertion direction of the medical instrument. The first and second indications 1005 and 1010 may provide information to the user related to the suitability of the position of the distal end 910 of the medical instrument for taking a biopsy along the current insertion direction of the medical instrument. In other embodiments, the first indication 1005 may represent the distance between distal end 910 of the medical instrument and the densest location within the target 920. In the illustrated embodiment, the system may further render a text label "Ti" indicating the position of the target 920.

The system may also render a graphical indicator 1015 over the rendered model. For example, the system may cause, based on the position and orientation of the distal end 910 of the medical instrument, a rendering of a graphical indicator 1015 extending from the distal end 910 of the medical instrument in the current insertion direction of the medical instrument. In certain embodiments, the system may render the graphical indicator in response to the distal end 910 of the medical instrument being within a threshold distance of the target 920. The system may also determine, based on the data from the at least one sensor, a change in at least one of the position and orientation of the distal end 910 of the medical instrument and, in response to determining the change in at least one of the position and orientation of the distal end 910 of the medical instrument, the system may determine that the graphical indicator 1015 intersects the target 920.

The system may cause a rendering of a change to the graphical indicator 1015 in response to determining that the line intersects the target 920. In one example, the system may change the color of the graphical indicator 1015 based on whether the graphical indicator 1015 intersects a portion of the target 920. This change in color may provide the user with a visual indication that the insertion direction is aligned with the target 920. When the medical instrument is aligned with the target 920 and within a threshold distance of the target 920, a medical tool may be deployed from the distal end 910 of the medical instrument to, for example, take a biopsy of the target 920.

The system may also change the color of the graphical indicator 1015 in response to the graphical indicator 1015 intersecting a specific portion of the target 920. For example, the user may select a portion of the target 920 for a biopsy or may select the center of the target 920 for biopsy. Thus, when the graphical indictor 1015 intersects the selected portion of the target 920, the system may change the displayed color of the graphical indictor 1015 to signal that the medical instrument may be positioned for biopsy of the selected region of the target 920. In certain cases, the target 920 may also have a non-uniform shape including larger, main body portion, and a smaller, secondary body portion joined to the main body portion. The main body portion may have a larger volume than the secondary body portion. When the secondary body portion has a volume that is less than a threshold volume, it may be impractical to align the medical instrument to take a biopsy of the secondary body portion. Accordingly, the system may define the center of the target 920 with respect to a center of the main body portion. The system may then change the color of the graphical indicator 1015 in response to the graphical indicator 1015 intersecting the center of the main body portion.

Figure 32:
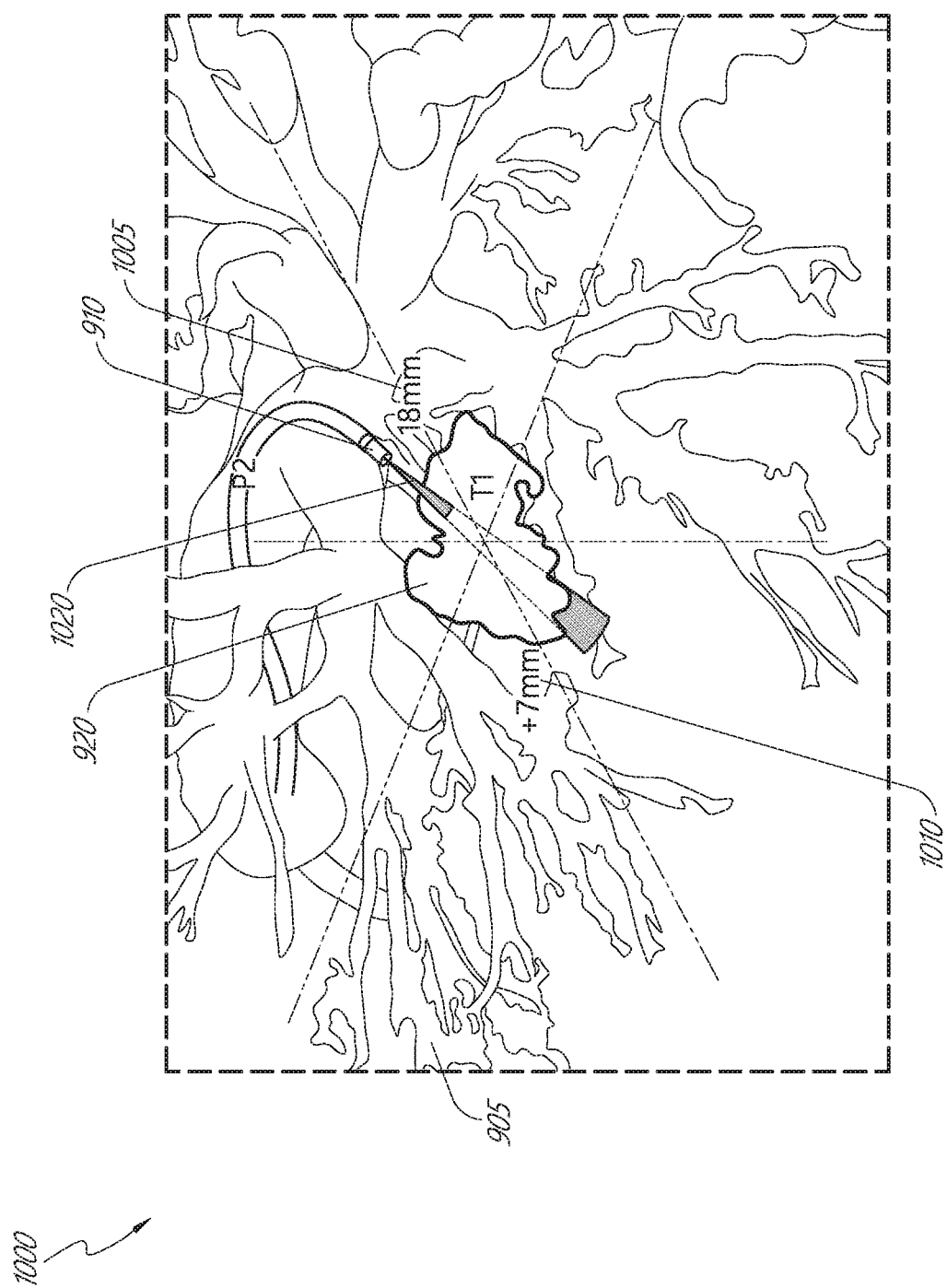
FIG. 32 is another example of a view which may be rendered on a display during a medical procedure in accordance with aspects of this disclosure.

In the embodiment illustrated in FIG. 31, the graphical indicator 1015 may be a line extending from the distal end 910 of the medical instrument. However, it is to be appreciated that in other embodiments, the graphical indicator may be a cylinder, a cone, a projected point or other shape on a surface pointed at by the medical instrument, or any other suitable indicator. Further, each of these indicators may be rendered using any suitable coloring, shading, or pattern (e.g., dotted or dashed lines). FIG. 32 is another example of a rendered view with a cone graphical indicator which may be displayed during a medical procedure in accordance with aspects of this disclosure. As just mentioned, in the embodiment of FIG. 32, the graphical indicator 1020 is a cone. The cone may be formed with an angle defining an aperture of the cone, where the aperture is based on an estimated error ranges of the orientation of the distal end 910 of the medical instrument. As used herein, the aperture of the cone may generally refer to the maximum angle between sides of the cone or twice the angle between the axis of the cone and a side of the cone. For example, the system may be able to determine an estimated error of the orientation of the distal end 910 of the medical instrument based on EM data detected using one or more EM sensors located on the medical instrument. The error in the measured orientation may thus be communicated to the user by altering the aperture of the cone based on the estimated error. In other embodiments, the aperture of the cone 1020 may relate to (and be adjusted according to) the distance between the distal end 910 of the medical instrument and the target 920. For example, the aperture of the cone may decrease in size as the distance between the distal end 910 of the medical instrument and the target 920 decreases.

3. Implementing Systems and Terminology.

Implementations disclosed herein provide systems, methods and apparatuses for medical instrument navigation and targeting.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The modelling and/or rendering functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system, comprising:
a medical instrument having an elongate body and at least one sensor;
a display;
a processor; and
a memory storing computer-executable instructions to cause the processor to:
access a three-dimensional model of a luminal network, the model based on a preoperative mapping of a portion of the luminal network,
determine a position of a target with respect to the model,
determine, based on data from the at least one sensor, a position and orientation of a distal end of the medical instrument with respect to the model,
cause, on at least a portion of the display, a rendering of the model, the position of the target with respect to the model, and the position and orientation of the distal end of the medical instrument with respect to the model, wherein the rendering comprises a virtual viewpoint directed at the target, the rendering being simulated from a virtual viewpoint perspective at a virtual location with respect to the model, and
cause within the portion of the display a rendering of a modified view of the model, the modified view being rendered from a modified virtual viewpoint in which the virtual viewpoint perspective is rotated around the target with the target as a center of the rotation.

2. The system of claim 1, further comprising a user input element, wherein the memory further stores computer-executable instructions to cause the processor to:
receive, via the user input element, a first type of user interaction with the user input element,
generate a first type of rendering instruction based on the first type of user interaction with the user input element, and
in response to generating the first type of rendering instruction, cause within the portion of the display the rendering of the modified view of the model, the position of the target, and the position and orientation of the distal end of the medical instrument.

3. The system of claim 2, wherein:
the first type of rendering instruction comprises a rotation instruction to rotate the viewpoint directed at the target, and
the modified view being rendered from the modified virtual viewpoint in which the virtual viewpoint perspective is rotated around the target with the target as the center of the rotation is performed in response to the rotation instruction.

4. The system of claim 2, wherein the memory further stores computer-executable instructions to cause the processor to:
receive, via the user input element, a second type of user interaction with the user input element,
generate a second type of rendering instruction based on the second type of user interaction with the user input element, the second type of rendering instruction comprising an elevation instruction to alter an angle between a reference plane centered at the target and the viewpoint directed at the target, and
in response to generating the second type of rendering instruction, cause within the portion of the display a rendering of the of the model having an altered the angle between the reference plane and the viewpoint directed at the target.

5. The system of claim 4, wherein:
the user input element comprises a button,
the first user interaction type comprises an actuation of the button for a greater than a threshold period of time, and
the second user interaction type comprises an actuation of the button for less than the threshold period of time.

6. The system of claim 2, wherein:
the first type of rendering instruction comprising a toggle perspective instruction to toggle the viewpoint of the rendering from the viewpoint different from the viewpoint of the medical instrument to the viewpoint of the medical instrument, and
the modified view comprises a rendering of the model from the viewpoint of the medical instrument.

7. The system of claim 1, wherein the memory further stores computer-executable instructions to cause the processor to:
cause, based on the position and orientation of the distal end of the medical instrument, a rendering of a graphical indicator extending from the distal end of the medical instrument in an insertion direction of the medical instrument,
determine, based on the data from the at least one sensor, a change in at least one of the position and orientation of the distal end of the medical instrument,
determine, in response to determining the change in at least one of the position and orientation of the distal end of the medical instrument, that the graphical indicator intersects the target, and
cause a rendering of a change to the graphical indicator in response to determining that the line intersects the target.

8. The system of claim 1, wherein the memory further stores computer-executable instructions to cause the processor to:
determine, based on the data from the at least one sensor, that the distal end of the medical instrument is within a threshold distance from the target; and
cause a rendering of a graphical indicator in response to determining that the distal end of the medical instrument is within a threshold distance from the target, the graphical indicator extending from the distal end of the medical instrument in an insertion direction of the medical instrument.

9. The system of claim 8, wherein the graphical indicator is selected from: a line, a cylinder, or a cone.

10. The system of claim 8, wherein the graphical indicator is a cone, the aperture of the cone is based on an estimated error range of the orientation of the distal end of the medical instrument.

11. The system of claim 8, wherein the memory further stores computer-executable instructions to cause the processor to:
determine, in response to determining the change in at least one of the position and orientation of the distal end of the medical instrument, that the graphical indicator intersects a center of the target, and
cause a rendering of a change in the color of the graphical indicator in response to determining that the graphical indicator intersects the center of the target.

12. The system of claim 1, wherein:
the model comprises a skeleton comprising a plurality of segments, wherein each of the segments is defined with respect to a center line of a corresponding lumen of the mapped portion of the luminal network,
the memory further stores computer-executable instructions to cause the processor to:
identify a segment in which the distal end of the medical instrument is located,
determine a depth of the distal end of the medical instrument along the identified segment, and
determine the position of the distal end of the medical instrument based on the identified segment and the depth.

13. The system of claim 12, wherein the memory further stores computer-executable instructions to cause the processor to:
determine a distance between the distal end of the medical instrument and the target based on the determined position of the distal end of the medical instrument and the position of the target.

14. The system of claim 12, wherein the memory further stores computer-executable instructions to cause the processor to:
determine that the position of the distal end of the medical instrument is within a volume defined by the model, and
restrict the determined position of the distal end of the medical instrument to be located along the skeleton.

15. The system of claim 12, wherein:
the at least one sensor comprises one of: an electromagnetic (EM) sensor or a shape sensing fiber, and
the memory further stores computer-executable instructions to cause the processor to configured generate the position data based only on data received from one of the EM sensor of the shape sensing fiber.

16. A non-transitory computer readable storage medium having stored thereon instructions that, when executed, cause at least one computing device to:
access a three-dimensional model of a luminal network, the model based on a preoperative mapping of a portion of the luminal network;
determine a position of a target with respect to the model;
determine, based on data from at least one sensor of a medical instrument, a position and orientation of a distal end of the medical instrument with respect to the model;
cause, on at least a portion of a display, a rendering of the model, a position of the target with respect to the model, and the position and orientation of the distal end of the medical instrument with respect to the model, wherein the rendering comprises a virtual viewpoint directed at the target, the rendering being simulated from a virtual viewpoint perspective at a virtual location with respect to the model; and
cause within the portion of the display a rendering of a modified view of the model, the modified view being rendered from a modified virtual viewpoint in which the virtual viewpoint perspective is rotated around the target with the target as a center of the rotation.

17. The non-transitory computer readable storage medium of claim 16, further having stored thereon instructions that, when executed, cause at least one computing device to:
receive, via the user input element, a first type of user interaction with the user input element;
generate a first type of rendering instruction based on the first type of user interaction with the user input element; and
in response to generating the first type of rendering instruction, cause within the portion of the display the rendering of the modified view of the model, the position of the target, and the position and orientation of the distal end of the medical instrument.

18. The non-transitory computer readable storage medium of claim 17, wherein:
the first type of rendering instruction comprises a rotation instruction to rotate the viewpoint directed at the target, and
the modified view being rendered from the modified virtual viewpoint in which the virtual viewpoint perspective is rotated around the target with the target as the center of the rotation is performed in response to the rotation instruction.

19. The non-transitory computer readable storage medium of claim 17, further having stored thereon instructions that, when executed, cause at least one computing device to:
receive, via the user input element, a second type of user interaction with the user input element;
generate a second type of rendering instruction based on the second type of user interaction with the user input element, the second type of rendering instruction comprising an elevation instruction to alter an angle between a reference plane centered at the target and the viewpoint directed at the target; and
in response to generating the second type of rendering instruction, cause within the portion of the display a rendering of the of the model having an altered the angle between the reference plane and the viewpoint directed at the target.

20. The non-transitory computer readable storage medium of claim 19, wherein:
the user input element comprises a button,
the first user interaction type comprises an actuation of the button for a greater than a threshold period of time, and
the second user interaction type comprises an actuation of the button for less than the threshold period of time.

21. The non-transitory computer readable storage medium of claim 17, wherein:
the first type of rendering instruction comprising a toggle perspective instruction to toggle the viewpoint of the rendering from the viewpoint different from the viewpoint of the medical instrument to the viewpoint of the medical instrument, and
the modified view comprises a rendering of the of the model from the viewpoint of the medical instrument.

22. The non-transitory computer readable storage medium of claim 16, further having stored thereon instructions that, when executed, cause at least one computing device to:
cause, based on the position and orientation of the distal end of the medical instrument, a rendering of a graphical indicator extending from the distal end of the medical instrument in an insertion direction of the medical instrument;
determine, based on the data from the at least one sensor, a change in at least one of the position and orientation of the distal end of the medical instrument;
determine, in response to determining the change in at least one of the position and orientation of the distal end of the medical instrument, that the graphical indicator intersects the target; and
cause a rendering of a change to the graphical indicator in response to determining that the line intersects the target.

23. The non-transitory computer readable storage medium of claim 16, further having stored thereon instructions that, when executed, cause at least one computing device to:

determine, based on the data from the at least one sensor, that the distal end of the medical instrument is within a threshold distance from the target; and cause a rendering of a graphical indicator in response to determining that the distal end of the medical instrument is within a threshold distance from the target, the graphical indicator extending from the distal end of the medical instrument in an insertion direction of the medical instrument.

24. The non-transitory computer readable storage medium of claim 23, further having stored thereon instructions that, when executed, cause at least one computing device to:

determine, in response to determining the change in at least one of the position and orientation of the distal end of the medical instrument, that the graphical indicator intersects a center of the target, and cause a rendering of a change in the color of the graphical indicator in response to determining that the graphical indicator intersects the center of the target.

25. The non-transitory computer readable storage medium of claim 24, wherein:

the model comprises a skeleton comprising a plurality of segments, wherein each of the segments is defined with respect to a center line of a corresponding lumen of the mapped portion of the luminal network, the non-transitory computer readable storage medium further has stored thereon instructions that, when executed, cause at least one computing device to:

identify a segment in which the distal end of the medical instrument is located;

determine a depth of the distal end of the medical instrument along the identified segment; and determine the position of the distal end of the medical instrument based on the identified segment and the depth.

26. The non-transitory computer readable storage medium of claim 25, further having stored thereon instructions that, when executed, cause at least one computing device to:

determine a distance between the distal end of the medical instrument and the target based on the determined position of the distal end of the medical instrument and the position of the target.

27. The non-transitory computer readable storage medium of claim 25, further having stored thereon instructions that, when executed, cause at least one computing device to:

cause, on at least another portion of the display, a rendering of the position of the distal end of the medical instrument based on the determined position of the distal end of the medical instrument.

28. The non-transitory computer readable storage medium of claim 25, further having stored thereon instructions that, when executed, cause at least one computing device to:

determine that the position of the distal end of the medical instrument is within a volume defined by the model, and restrict the determined position of the distal end of the medical instrument to be located along the skeleton.

29. The non-transitory computer readable storage medium of claim 25, wherein:

the at least one sensor comprises one of: an electromagnetic (EM) sensor or a shape sensing fiber, and the memory further stores computer-executable instructions to cause the processor to configured generate the position data based only on data received from one of the EM sensor of the shape sensing fiber.

30. The system of claim 2, wherein the memory further stores computer-executable instructions to cause the processor to:

receive, via the user input element, a second type of user interaction with the user input element, generate a second type of rendering instruction based on the second type of user interaction with the user input element, the second type of rendering instruction comprising toggle instruction to toggle between: (i) the virtual viewpoint positioned at a virtual location different from the position of the distal end of the medical instrument and (ii) a virtual viewpoint positioned at a virtual location that is the same as the position of the distal end of the medical instrument, and in response to generating the second type of rendering instruction, cause within the portion of the display a rendering of the of the model from the virtual viewpoint positioned at the virtual location that is the same as the position of the distal end of the medical instrument.

* * * * *